(12) United States Patent
Seitz et al.

(10) Patent No.: US 8,481,456 B2
(45) Date of Patent: Jul. 9, 2013

(54) ACTIVE COMPOUND COMBINATIONS

(75) Inventors: Thomas Seitz, Langenfeld (DE); Ulrike Wachendorff-Neumann, Neuwied (DE); Heike Hungenberg, Langenfeld (DE); Peter Dahmen, Neuss (DE)

(73) Assignee: Bayer CropScience AG, Monheim (DE)

( * ) Notice: Subject to any disclaimer, the term of this patent is extended or adjusted under 35 U.S.C. 154(b) by 269 days.

(21) Appl. No.: 12/947,961

(22) Filed: Nov. 17, 2010

(65) Prior Publication Data

US 2011/0118115 A1 May 19, 2011

Related U.S. Application Data

(60) Provisional application No. 61/262,258, filed on Nov. 18, 2009.

(30) Foreign Application Priority Data

Nov. 17, 2009 (EP) .................................. 09176210
Dec. 17, 2009 (EP) .................................. 09179614

(51) Int. Cl.
| | | |
|---|---|---|
| *A01N 43/40* | (2006.01) | |
| *A01N 43/78* | (2006.01) | |
| *A01N 43/90* | (2006.01) | |
| *A01N 43/32* | (2006.01) | |
| *A01N 43/38* | (2006.01) | |
| *A01N 47/40* | (2006.01) | |
| *A01N 47/44* | (2006.01) | |
| *A01N 51/00* | (2006.01) | |
| *A01P 3/00* | (2006.01) | |
| *A01P 7/04* | (2006.01) | |

(52) U.S. Cl.
USPC ........ 504/100; 514/229.2; 514/341; 514/342; 514/357; 514/365; 514/411

(58) Field of Classification Search
USPC ............... 504/100; 514/229.2, 341, 342, 357, 514/365, 411
See application file for complete search history.

(56) References Cited

U.S. PATENT DOCUMENTS

| | | | |
|---|---|---|---|
| 3,364,229 A | 1/1968 | Draber et al. | |
| 4,245,432 A | 1/1981 | Dannelly | |
| 4,272,417 A | 6/1981 | Barke et al. | |
| 4,808,430 A | 2/1989 | Kouno | |
| 4,845,106 A * | 7/1989 | Shiokawa et al. | 514/342 |
| 5,034,404 A * | 7/1991 | Uneme et al. | 514/365 |
| 5,876,739 A | 3/1999 | Turnblad et al. | |
| 2003/0069242 A1 | 4/2003 | Toriyabe et al. | |
| 2003/0176428 A1 | 9/2003 | Schneidersmann et al. | |
| 2008/0305955 A1 | 12/2008 | Bretschneider et al. | |
| 2009/0247551 A1 | 10/2009 | Jeschke et al. | |
| 2009/0253749 A1 | 10/2009 | Jeschke et al. | |
| 2010/0120884 A1 | 5/2010 | Seitz et al. | |
| 2010/0240705 A1 | 9/2010 | Jeschke et al. | |
| 2011/0064827 A1 * | 3/2011 | Seitz et al. | 424/633 |
| 2011/0257009 A1 | 10/2011 | Seitz et al. | |

FOREIGN PATENT DOCUMENTS

| | | |
|---|---|---|
| CA | 2 671 179 A1 | 6/2008 |
| WO | WO 89/10396 A1 | 11/1989 |
| WO | WO 96/33270 A1 | 10/1996 |
| WO | WO 02/28186 A2 | 4/2002 |
| WO | WO 02/080675 A1 | 10/2002 |
| WO | WO 2007/024782 A2 | 3/2007 |
| WO | WO 2007/095229 A2 | 8/2007 |
| WO | WO 2007/149134 A1 | 12/2007 |

OTHER PUBLICATIONS

Office Action in U.S. Appl. No. 13/086,921, filed Apr. 14, 2011, Seitz et al., mailed Dec. 20, 2012.
Bauer, T.A., et al., "Response of Selected Weed Species to Postemergence Imazethapyr and Bentazon," *Weed Tech.* 9:236-242, The Weed Science Society of America, United States (1995).
Blackshaw, R.E., "HOE-39866 Use in Chemical Fallow Systems," *Weed Tech.* 3:420-428, The Weed Science Society of America, United States (1989).
Blackshaw, R.E., "Synergistic Mixes of DPX-A7881 and Clopyralid in Canola (*Brassica napus*)," *Weed Tech.* 3:690-695, The Weed Science Society of America, United States (1989).
Blackshaw, R.E., et al., "Herbicide Combinations for Postemergent Weed Control in Safflower (*Carthamus tinctorius*)," *Weed Tech.* 4:97-104, The Weed Science Society of America, United States (1990).
Blouin, D.C., et al., "Analysis of Synergistic and Antagonistic Effects of Herbicides Using Nonlinear Mixed-Model Methodology," *Weed Tech.* 18:464-472, The Weed Science Society of America, United States (2004).
Bradley, P.R., et al., "Response of Sorghum (*Sorghum bicolor*) to Atrazine, Ammonium Sulfate, and Glyphosate," *Weed Tech.* 14:15-18, The Weed Science Society of America, United States (2000).
Buker, III, R.S., et al., "Confirmation and Control of a Paraquat-Tolerant Goosegrass (*Eleusine indica*) Biotype," *Weed Tech.* 16:309-313, The Weed Science Society of America, United States (2002).
Burke, I.C., et al., "CGA-362622 Antagonizes Annual Grass Control with Clethodim," *Weed Tech.* 16:749-754, The Weed Science Society of America, United States (2002).
Colby, S.R., "Calculating Synergistic and Antagonistic Response to Herbicide Combinations," *Weeds* 15:20-22, Weed Society of America, United States (1967).
Draber, W., "Chemie der Pflanzenschutz-und Schadlingsbekampfungsmittel [Chemistry of Plant Protection and Pest Control Agents]," *R. Wegler ed.* 2:400-412, Springer-Verlag, Berlin, Germany (1970).
Draber, W., "Chemie der Pflanzenschutz-und Schadlingsbekampfungsmittel [Chemistry of Plant Protection and Pest Control Agents]," *R. Wegler ed.* 2:1-15, Springer-Verlag, Berlin, Germany (1970) (English Translation).

(Continued)

*Primary Examiner* — John Pak
(74) *Attorney, Agent, or Firm* — Sterne, Kessler, Goldstein & Fox P.L.L.C.

(57) ABSTRACT

Active compound combinations are disclosed which comprise (A) a dithiino-tetracarboximide of formula (I) and a further insecticidally active compound (B). Methods for controlling animal pests such as insects and/or unwanted acarids and for curatively or preventively controlling the phytopathogenic fungi of plants or crops are also disclosed as well as the use of a composition according to the invention for the treatment of seed, to a method for protecting a seed and to the treated seed.

17 Claims, No Drawings

OTHER PUBLICATIONS

Flint, J.L., et al., "Analyzing Herbicide Interactions: A Statistical Treatment of Colby's Method," *Weed Tech.* 2:304-39, The Weed Science Society of America, United States (1988).

Gillespie, G.R., et al., "Wheat (*Triticum aestivum*) Response to Triallate Plus Chlorsulfuron," *Weed Tech.* 3:20-23, The Weed Science Society of America, United States (1989).

Green, J.M., et al., "Metribuzin and Chlorimuron Mixtures for Preemergence Broadleaf Weed Control in Soybeans, *Glycine max*," *Weed Tech.* 2:355-363, The Weed Science Society of America, United States (1988).

Harker, K.N., et al., "Synergistic Mixtures of Sethoxydim and Fluazifop on Annual Grass Weeds," *Weed Tech.* 5:310-316, The Weed Science Society of America, United States (1991).

Kent, L.M., et al., "Effect of Ammonium Sulfate, Imazapyr, and Environment on the Phytotoxicity of Imazethapyr," *Weed Tech.* 5:202-205, The Weed Science Society of America, United States (1991).

Kotoula-Syka, E., et al., "Interactions between SAN 582H and Selected Safeners on Grain Sorghum (*Sorghum bicolor*) and Corn (*Zea mays*)," *Weed Tech.* 10:299-304, The Weed Science Society of America, United States (1996).

Lanclos, D.Y., et al., "Glufosinate Tank-Mix Combinations in Glufosinate-Resistant Rice (*Oryza sativa*),"*Weed Tech.* 16:659-663, The Weed Science Society of America, United States (1996).

Norris, J.L., et al., "Weed Control from Herbicide Combinations with Three Formulations of Glyphosate," *Weed Tech.* 15:552-558, The Weed Science Society of America, United States (2001).

Novosel, K.M., et al., "Metolachlor Efficacy as Influenced by Three Acetolactate Synthase-Inhibiting Herbicides," *Weed Tech.* 12:248-253, The Weed Science Society of America, United States (1998).

Palmer, E.W., et al., "Broadleaf Weed Control in Soybean (*Glycine max*) with CGA-277476 and Four Postemergence Herbicides," *Weed Tech.* 14:617-623, The Weed Science Society of America, United States (2000).

Rummens, F.H.A., "An Improved Definition of Synergistic adn Antagonistic Effects," *Weed Science* 23;4-6, The Weed Science Society of America, United States (1975).

Salzman, F.P and Renner, K.A., "Response of Soybean to Combinations of Clomazone, Metribuzin, Linuron, Alachlor, and Atrazine," *Weed Tech.* 6:922-929, The Weed Science Society of America, United States (1992).

Scott, R.C., et al., "Spray Adjucant, Formulation, and Environmental Effects on Synergism from Post-Applied Tank Mixtures of SAN 582H with Fluazifop-P, Imazethapyr, and Sethoxydim," *Weed Tech.* 12:463-469, The Weed Science Society of America, United States (1998).

Shaw, D.R. and Arnold, J.C., "Weed Control from Herbicide Combinations with Glyphosate," *Weed Tech.* 16:1-6, The Weed Science Society of America, United States (2002).

Snipes, C.E. and Allen, R.L., "Interaction of Graminicides Applied in Combination with Pyrithiobac," *Weed Tech.* 10:889-892, The Weed Science Society of America, United States (1996).

Sun, Y.-P., et al., "Analysis of Joint Action of Insecticides Against House Flies," *J. Econ. Entomol.* 53:887-892, Entomological Society of America, United States (1960).

Tammes, P.M.L., "Isoboles, a Graphic Representation of Synergism in Pesticides," *Neth. J. Plant Path.* 70:73-80, Springer, Germany (1964).

Wehtje, G. and Walker, R.H., "Interaction of Glyphosate and 2,4-DB for the Control fo Selected Morningglory (*Ipomoea* spp.) Species," *Weed Tech.* 11:152-156, The Weed Science Society of America, United States (1997).

Zentz, F., et al., "Syntheses, in vitro antibacterial and antifungal activities of a series of *N*-alkyl, 1,4-dithiines," *Il Farmaco* 60:944-947, Elsevier SAS, Italy (2005).

Zhang, W., et al.,"Fenoxaprop Interactions for Barnyardgrass (*Echinochloa crusgalli*) Control in Rice," *Weed Tech.* 19:293-297, The Weed Science Society of America, United States (2005).

Internation Search Report and Written Opinion for International Patent Application No. PCT/EP2010/067503, European Patent Office, Rijswijk, Netherlands, mailed on Apr. 19, 2011.

\* cited by examiner

ACTIVE COMPOUND COMBINATIONS

FIELD OF THE INVENTION

The present invention relates to active compound combinations, in particular within an insecticide or fungicide composition, which comprises (A) a dithiino-tetracarboximide of formula (I) and a further insectitidally active compound (B). Moreover, the invention relates to a method for controlling animal pests such as insects and/or unwanted acarids and for curatively or preventively controlling the phytopathogenic fungi of plants or crops, to the use of a combination according to the invention for the treatment of seed, to a method for protecting a seed and not at least to the treated seed.

BACKGROUND OF THE INVENTION

Dithiino-tetracarboximides as such are already known. It is also known, that these compounds can be used as anthelmintics and insecticides (cf. U.S. Pat. No. 3,364,229). Furthermore the fungicidal use of such dithiino-tetracarboximides is known (European Patent Application No. 08166621.6).

Since the environmental and economic requirements imposed on modern-day crop protection compositions are continually increasing, with regard, for example, to the spectrum of action, toxicity, selectivity, application rate, formation of residues, and favourable preparation ability, and since, furthermore, there may be problems, for example, with resistances, a constant task is to develop new compositions, in particular fungicidal agents, which in some areas at least help to fulfil the abovementioned requirements.

The present invention provides active compound combinations/compositions which in some aspects at least achieve the stated objective.

SUMMARY OF THE INVENTION

It has now been found, surprisingly, that the combinations according to the invention not only bring about the additive enhancement of the spectrum of action with respect to the pest and/or phytopathogen to be controlled that was in principle to be expected but achieves a synergistic effect which extends the range of action of the component (A) and of the component (B) in two ways. Firstly, the rates of application of the component (A) and of the component (B) may be lowered whilst the action remains equally good. Secondly, the combination still achieves a high degree of pest and/or phytopathogen control even where the two individual compounds have become totally ineffective in such a low application rate range. This allows, on the one hand, a substantial broadening of the spectrum of pests and/or phytopathogens that can be controlled and, on the other hand, increased safety in use.

In addition to the insecticidal, acaricidal and/or fungicidal synergistic activity, the active compound combinations according to the invention have further surprising properties which, in a wider sense, may also be called synergistic, such as, for example: broadening of the activity spectrum to other pest ancUorphytopathogens, for example to resistant strains of plant diseases; lower application rates of the active compounds; sufficient control of pests with the aid of the active compound combinations according to the invention even at application rates where the individual compounds show no or virtually no activity; advantageous behaviour during formulation or during use, for example during grinding, sieving, emulsifying, dissolving or dispensing; improved storage stability and light stability; advantageous residue formation; improved toxicological or ecotoxicological behaviour; improved properties of the plant, for example better growth, increased harvest yields, a better developed root system, a larger leaf area, greener leaves, stronger shoots, less seed required, lower phytotoxicity, mobilization of the defense system of the plant, good compatibility with plants. Thus, the use of the active compound combinations or compositions according to the invention contributes considerably to keeping young cereal stands healthy, which increases, for example, the winter survival of the cereal seed treated, and also safeguards quality and yield. Moreover, the active compound combinations according to the invention may contribute to enhanced systemic action. Even if the individual compounds of the combination have no sufficient systemic properties, the active compound combinations according to the invention may still have this property. In a similar manner, the active compound combinations according to the invention may result in higher persistency of the fungicidal action.

Accordingly, the present invention provides a combination comprising:

(A) at least one dithiino-tetracarboximide of formula (I)

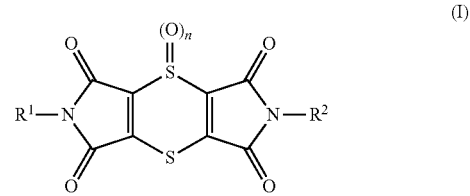

in which $R^1$ and $R^2$ are identical and represent methyl, ethyl, n-propyl or isopropyl, and n represents 0 or 1, or an agrochemically acceptable salt thereof, and (B) at least one further active compound selected from the following groups
  (1) acetylcholinesterase (AChE) inhibitors,
  (2) GABA-gated chloride channel antagonists,
  (3) sodium channel modulators/voltage-dependent sodium channel blockers,
  (4) nicotinergic acetylcholine receptor agonists,
  (5) allosteric acetylcholine receptor modulators (agonists),
  (6) chloride channel activators,
  (7) juvenile hormone mimics,
  (8) miscellaneous non-specific (multi-site) inhibitors,
  (9) selective homopteran feeding blockers,
  (10) mite growth inhibitors,
  (11) microbial disruptors of insect midgut membranes,
  (12) inhibitors of mitochondrial ATP synthase,
  (13) uncouplers of oxidative phoshorylation via disruption of the proton gradient,
  (14) nicotinic acetylcholine receptor channel blockers,
  (15) inhibitors of chitin biosynthesis (type 0),
  (16) inhibitors of chitin biosynthesis (type 1),
  (17) moulting disruptors,
  (18) ecdysone receptor agonists/disruptors,
  (19) octopamine receptor agonists,
  (20) mitochondrial complex III electron transport inhibitors,
  (21) mitochondrial complex I electron transport inhibitors,
  (22) voltage-dependent sodium channel blockers,
  (23) inhibitors of acetyl CoA carboxylase,
  (24) mitochondrial complex IV electron inhibitors,
  (25) mitochondrial complex II electron transport inhibitors,
  (26) ryanodine receptor modulators,
  (27) other insecticides.

DETAILED DESCRIPTION OF THE INVENTION

Preference is given to combinations comprising at least one compound of the formula (I) selected from the group consisting of (I-1) 2,6-dimethyl-1H,5H-[1,4]dithiino[2,3-c:5,6-c'] dipyrrole-1,3,5,7(2H,6H)-tetrone (i.e. $R^1=R^2$=methyl, n=0)

(I-2) 2,6-diethyl-1H,5H-[1,4]dithiino[2,3-c:5,6-c']dipyrrole-1,3,5,7(2H,6H)-tetrone (i.e. $R^1=R^2$=ethyl, n=0)

(I-3) 2,6-dipropyl-1H,5H-[1,4]dithiino[2,3-c:5,6-c']dipyrrole-1,3,5,7(2H,6H)-tetrone (i.e. $R^1=R^2$=n-propyl, n=0)

(I-4) 2,6-diisopropyl-1H,5H-[1,4]dithiino[2,3-c:5,6-c'] dipyrrole-1,3,5,7(2H,6H)-tetrone (i.e. $R^1=R^2$=isopropyl, n=0)

(I-5) 2,6-dimethyl-1H,5H-[1,4]dithiino[2,3-c:5,6-c'] dipyrrole-1,3,5,7(2H,6H)-tetrone 4-oxide (i.e. $R^1=R^2$=methyl, n=1)

Preference is further given to combinations comprising an acetylcholinesterase (AChE) inhibitor selected from the group consisting of [Group (1)]:

Group (1A): carbamates, e.g. (1A.1) alanycarb, (1A.2) aldicarb, (1A.3) bendiocarb, (1A.4) benfuracarb, (1A.5) butocarboxim, (1A.6) butoxycarboxim, (1A.7) carbaryl, (1A.8) carbofuran, (1A.9) carbosulfan, (1A.10) ethiofencarb, (1A.11) fenobucarb, (1A.12) formetanate, (1A.13) furathiocarb, (1A.14) isoprocarb, (1A.15) methiocarb, (1A.16) methomyl, (1A.17) metolcarb, (1A.18) oxamyl, (1A.19) pirimicarb, (1A.20) propoxur, (1A.21) thiodicarb, (1A.22) thiofanox, (1A.23) triazamate, (1A.24) trimethacarb, (1A.25) XMC, and (1A.26) xylylcarb; or Group (1B) organophosphates, e.g. (1B.1) acephate, (1B.1) azamethiphos, (1B.2) azinphos, (1B.3) azinphos-methyl, (1B.4) azinphos-ethyl, (1B.5) cadusafos, (1B.6) chlorethoxyfos, (1B.7) chlorfenvinphos, (1B.8) chlorfenvinphos, (1B.9) chlormephos, (1B.10) chlorpyrifos, (1B.11) chlropyrifos-methyl, (1B.12) coumaphos, (1B.13) cyanophos, (1B.14) demeton-5-methyl, (1B.15) diazinon, (1B.16) dichlorvos/DDVP, (1B.17) dicrotophos, (1B.18) dimethoate, (1B.19) dimethylvinphos, (1B.20) disulfoton, (1B.21) EPN, (1B.22) ethion, (1B.23) ethoprophos, (1B.24) famphur, (1B.25) fenamiphos, (1B.26) fenitrothion, (1B.27) fenthion, (1B.28) fosthiazate, (1B.29) heptenophos, (1B.30) isofenphos, (1B.31) isopropyl 0-(methoxy-aminothio-phosphoryl) salicylate, (1B.32) isoxathion, (1B.33) malathion, (1B.34) mecarbam, (1B.35) methamidophos, (1B.36) methidathion, (1B.37) mevinphos, (1B.38) monocrotophos, (1B.39) naled, (1B.40) omethoate, (1B.41) oxydemeton-methyl, (1B.42) parathion, (1B.43) parathion-methyl, (1B.44) phenthoate, (1B.45) phorate, (1B.46) phosalone, (1B.47) phosmet, (1B.48) phosphamidon, (1B.49) phoxim, (1B.50) pirimiphos, (1B.51) pirimiphos-methyl, (1B.52) profenofos, (1B.53) propetamphos, (1B.54) prothiofos, (1B.55) pyraclofos, (1B.56) pyridaphenthion, (1B.57) quinalphos, (1B.58) sulfotep, (1B.59) tebupirimfos, (1B.60) temephos, (1B.61) terbufos, (1B.62) tetrachlorvinphos, (1B.63) thiometon, (1B.64) triazophos, (1B.65) triclorfon, and (1B.66) vamidothion.

Particular preference is given to combinations comprising an acetylcholinesterase (AChE) inhibitor selected from the group consisting of (1A.15) methiocarb, (1A.21) thiodicarb.

Preference is further given to combinations comprising a GABA-gated chloride channel antagonist selected from the group consisting of [Group (2)]:

Group (2A): organochlorines, e.g. (2A.1) chlordane, (2A.2) endosulfan, (2A.3) alpha-endosulfan; or Group (2B): fiproles (phenylpyrazoles), e.g. (2B.1) ethiprole, (2B.2) fipronil, (2B.3) pyrafluprole, and (2B.4) pyriprole.

Particular preference is given to combinations comprising a GABA-gated chloride channel antagonist selected from the group consisting of (2B.1) ethiprole, (2B.2) fipronil.

Preference is further given to combinations comprising a sodium channel modulators/voltage-dependent sodium channel blocker selected from the group consisting of [Group (3)]:

Group (3A): pyrethroids, e.g. (3A.1) acrinathrin, (3A.2) allethrin, (3A.3) d-cis-trans-allethrin, (3A.4) d-trans-allethrin, (3A.5) bifenthrin, (3A.6) bioallethrin, (3A.7) bioallethrin S-cyclopentenyl, (3A.8) bioresmethrin, (3A.9) cycloprothrin, (3A.10) cyfluthrin, (3A.11) β-cyfluthrin, (3A.12) cyhalothrin, (3A.13) γ-cyhalothrin, (3A.14) λ-cyhalothrin, (3A.15) cypermethrin, (3A.16) α-cypermethrin, (3A.17) β-cypermethrin, (3A.18) θ-cypermethrin, (3A.19) ζ-cypermethrin, (3A.20) cyphenothrin [(1R)-trans-isomers], (3A.21) deltamethrin, (3A.22) dimefluthrin, (3A.23) empenthrin [(EZ)-(1R)-isomers)], (3A.24) esfenvalerate, (3A.25) etofenprox, (3A.26) fenpropathrin, (3A.27) fenvalerate, (3A.28) flucythrinate, (3A.29) flumethrin, (3A.30) fluvalinate, (3A.31) tau-fluvalinate, (3A.32) halfenprox, (3A.33) imiprothrin, (3A.34) metofluthrin, (3A.35) permethrin, (3A.36) phenothrin [(1R)-trans-isomer)], (3A.37) prallethrin, (3A.38) profluthrin, (3A.39) pyrethrin (pyrethrum), (3A.40) resmethrin, (3A.41) RU 15525, (3A.42) silafluofen, (3A.43) tefluthrin, (3A.44) tetramethrin [(1R)-isomers)], (3A.45) tralomethrin, (3A.46) transfluthrin and (3A.47) ZXI 8901; or Group (3B): (3B.1) DDT or (3B.2) methoxychlor.

Particular preference is given to combinations comprising a sodium channel modulators/voltage-dependent sodium channel blocker selected from the group consisting of (3A.10) cyfluthrin, (3A.11) β-cyfluthrin, (3A.12) cyhalothrin, (3A.14) λ-cyhalothrin, (3A.46) transfluthrin.

Preference is further given to combinations comprising a nicotinergic acetylcholine receptor agonist selected from the group consisting of [Group (4)]:

Group (4A): chloronicotinyls, e.g. (4A.1) acetamiprid, (4A.2) clothianidin, (4A.3) dinotefuran, (4A.4) imidacloprid, (4A.5) nitenpyram, (4A.6) thiacloprid, (4A.7) thiamethoxam;

Group (4B): (4.B.1) nicotine.

Particular preference is given to combinations comprising a nicotinergic acetylcholine receptor agonist selected from the group consisting of (4A.1) acetamiprid, (4A.2) clothianidin, (4A.4) imidacloprid, (4A.6) thiacloprid, (4A.7) thiamethoxam.

Preference is further given to combinations comprising an allosteric acetylcholine receptor modulator (agonist) selected from the group consisting of [Group (5)]:

spinosyns, e.g. (5.1) spinetoram and (5.2) spinosad.

Preference is further given to combinations comprising a chloride channel activator selected from the group consisting of [Group (6)]:

avermectins/milbemycins, e.g. (6.1) abamectin, (6.2) emamectin benzoate, (6.3) lepimectin, and (6.4) milbemectin.

Particular preference is given to combinations comprising a chloride channel activator selected from the group consisting of (6.1) abamectin.

Preference is further given to combinations comprising a juvenile hormone mimic selected from the group consisting of [Group (7)]:

(7.1) hydroprene, (7.2) kinoprene, (7.3) methoprene; or (7.4) fenoxycarb; (7.5) pyriproxyfen Preference is further given to combinations comprising a miscellaneous non-specific (multi-site) inhibitor selected from the group consisting of [Group (8)]:

Group (8A): gassing agents, e.g. (8A.1) methyl bromide, (8A.2) other alkyl halides; or Group (8B): (8B.1) chloropicrin; (8B.2) sulfuryl fluoride; (8B.3) borax; (8B.4) tartar emetic.

Preference is further given to combinations comprising a selective homopteran feeding blocker selected from the group consisting of [Group (9)]:

(9.1) pymetrozine, (9.2) flonicamid.

Particular preference is given to combinations comprising a selective homopteran feeding blocker selected from the group consisting of (9.2) flonicamid.

Preference is further given to combinations comprising a mite growth inhibitor selected from the group consisting of [Group (10)]:

(10.1) clofentezine, (10.2) diflovidazin, (10.3) hexythiazox, (10.4) etoxazole.

Preference is further given to combinations comprising a microbial disruptor of insect midgut membranes selected from the group consisting of [Group (11)]:

(11.1) *Bacillus thuringiensis* subspecies *israelensis*, (11.2) *Bacillus sphaericus*, (11.3) *Bacillus thuringiensis* subspecies *aizawai*, (11.4) *Bacillus thuringiensis* subspecies *kurstaki*, (11.5) *Bacillus thuringiensis* subspecies *tenebrionis*, and BT crop proteins: (11.6) Cry1Ab, (11.7) Cry1Ac, (11.8) Cry1Fa, (11.9) Cry2Ab, (11.10) mCry3A, (11.11) Cry3Ab, (11.12) Cry3Bb, (11.13) Cry34/35Ab1.

Preference is further given to combinations comprising an inhibitor of mitochondrial ATP synthase selected from the group consisting of [Group (12)]:

Group (12A): (12A.1) diafenthiuron; or

Group (12B): organotin miticides, e.g. (12B.1) azocyclotin, (12B.2) cyhexatin, and (12B.3) fenbutatin oxide; or Group (12C): (12C.1) propargite; (12C.2) tetradifon.

Preference is further given to combinations comprising an uncoupler of oxidative phoshorylation via disruption of the proton gradient selected from the group consisting of [Group (13)]:

(13.1) chlorfenapyr, and (13.2) DNOC.

Preference is further given to combinations comprising a nicotinic acetylcholine receptor channel blocker selected from the group consisting of [Group (14)]:

(14.1) bensultap, (14.2) cartap hydrochloride, (14.3) thiocyclam, and (14.4) thiosultap-sodium.

Preference is further given to combinations comprising an inhibitor of chitin biosynthesis (type 0) selected from the group consisting of [Group (15)]:

benzoylureas, e.g. (15.1) bistrifluron, (15.2) chlorfluazuron, (15.3) diflubenzuron, (15.4) flucycloxuron, (15.5) flufenoxuron, (15.6) hexaflumuron, (15.7) lufenuron, (15.8) novaluron, (15.9) noviflumuron, (15.10) penfluoron, (15.11) teflubenzuron, and (15.12) triflumuron.

Preference is further given to combinations comprising an inhibitor of chitin biosynthesis (type 1) selected from the group consisting of [Group (16)]:

(16.1) buprofezin.

Preference is further given to combinations comprising a moulting disruptor selected from the group consisting of [Group (17)]:

(17.1) cyromazine.

Preference is further given to combinations comprising an ecdysone receptor agonist/disruptor selected from the group consisting of [Group (18)]:

diacylhydrazines, e.g. (18.1) chromafenozide, (18.2) halofenozide, (18.3) methoxyfenozide, and (18.4) tebufenozide.

Preference is further given to combinations comprising an octopamine receptor agonist selected from the group consisting of [Group (19)]:

(19.1) amitraz.

Preference is further given to combinations comprising a mitochondrial complex III electron transport inhibitor selected from the group consisting of [Group (20)]:

(20.1) Hydramethylnon, (20.2) acequinocyl, and (20.3) fluacrypyrim.

Preference is further given to combinations comprising a mitochondrial complex I electron transport inhibitor selected from the group consisting of [Group (21)]:

METI acaricides, e.g. (21.1) fenazaquin, (21.2) fenpyroximate, (21.3) pyrimidifen, (21.4) pyridaben, (21.5) tebufenpyrad, (21.6) tolfenpyrad or (21.7) rotenone.

Preference is further given to combinations comprising a voltage-dependent sodium channel blocker selected from the group consisting of [Group (22)]:

(22.1) indoxacarb; (22.2) metaflumizone.

Preference is further given to combinations comprising an inhibitor of acetyl CoA carboxylase selected from the group consisting of [Group (23)]:

Group 23A: tetronic acid derivatives, e.g. (23A.1) spirodiclofen and (23A.2) spiromesifen; or Group 23B: tetramic acid derivatives, e.g. (23B.1) spirotetramat.

Preference is further given to combinations comprising a mitochondrial complex IV electron inhibitor selected from the group consisting of [Group (24)]:

Group (24A): phosphines, e.g. (24A.1) aluminium phosphide, (24A.2) calcium phosphide, (24A.3) phosphine, and (24A.4) zinc phosphide or Group (24B): (23B.1) cyanide.

Preference is further given to combinations comprising a mitochondrial complex II electron transport inhibitor selected from the group consisting of [Group (25)]:

(25.1) cyenopyrafen.

Preference is further given to combinations comprising a ryanodine receptor modulator selected from the group consisting of [Group (26)]:

diamides, e.g. (26.1) chloranthraniliprole (rynaxypyr), (26.2) cyantraniliprole (cyazypyr), and (26.3) flubendiamide.

Preference is further given to combinations comprising an insecticide selected from the group consisting of [Group (27)]:

(27.1) azadirachtin, (27.2) amidoflumet, (27.3) benzoximate, (27.4) bifenazate, (27.5) chinomethionat, (27.6) cryolite, (27.7) cyflumetofen, (27.8) dicofol, (27.9) flufenerim, (27.10) pyridalyl, (27.11) pyrifluquinazon; (27.12) 4-{[(6-bromopyridin-3-yl)methyl](2-fluoroethyl)amino}furan-2(5H)-one, (27.13) 4-{[(6-fluoropyridin-3-yl)methyl](2,2-difluoroethyl)amino}furan-2(5H)-one, (27.14) 4-{[(2-chloro-1,3-thiazol-5-yl)methyl](2-fluoroethyl)amino}furan-2(5H)-one, (27.15) 4-{[(6-chloropyridin-3-yl)methyl](2-fluoroethyl)amino}furan-2(5H)-one, (27.16) 4-{[(6-chloropyridin-3-yl)methyl](2,2-difluoroethyl)amino}furan-2(5H)-one, (27.17) 4-{[(6-chloro-5-fluoropyridin-3-yl)methyl](methyl)amino}furan-2(5H)-one, (27.18) 4-{[(5,6-dichloropyridin-3-yl)methyl](2-fluoroethyl)amino}furan-2(5H)-one, (27.19) 4-{[(6-chloro-5-fluoropyridin-3-yl)methyl](cyclopropyl)amino}furan-2(5H)-one, (27.20) 4-{[(6-chloropyridin-3-yl)methyl](cyclopropyl)amino}furan-2(5H)-one, (27.21) 4-{[(6-chloropyridin-3-yl)methyl](methyl)amino}furan-2(5H)-one, (27.22) [(6-chloropyridin-3-yl)methyl](methyl)oxido-$\lambda^4$-sulfanylidenecyanamide, (27.23) [1-(6-chloropyridin-3-yl)ethyl](methyl)oxido-$\lambda^4$-sulfanylidenecyanamide and its diastereomeres (27.24) {[(1R)-1-(6-chloropyridin-3-yl)ethyl](methyl)oxido-$\lambda^6$-sulfanylidene}cyanamide and (27.25) {[(1S)-1-(6-chloropyridin-3-yl)ethyl](methyl)oxido-$\lambda^6$-sulfanylidene}cyanamide, (27.26) [(6-trifluoromethylpyridin-3-yl)methyl](methypoxido-$\lambda^4$-sulfanylidenecyanamide, or (27.27) sulfoxaflor, (27.28) 11-(4-chloro-2,6-dimethylphenyl)-12-hydroxy-1,4-dioxa-9-azadispiro[4.2.4.2]tetradec-11-en-10-one, (28.29) 3-(4'-fluoro-2,4-dimethylbiphenyl-3-yl)-4-hydroxy-8-oxa-1-azaspiro[4.5]dee-3-en-2-one, and (28.30) 1-{2,4-dimethyl- 5-[(2,2,2-trifluoroethyl)sulfinyl]phenyl}-3-(trifluoromethyl)-1H-1,2,4-triazole.

Particular preference is further given to combinations comprising an insecticide selected from the group consisting of (27.15) 4-{[(6-chloropyridin-3-yl)methyl](2-fluoroethyl)amino}furan-2(5H)-one, (27.16) 4-{[(6-chloropyridin-3-yl)methyl](2,2-difluoroethyl)amino}furan-2(5H)-one, (27.27) sulfoxaflor, (27.28) 11-(4-chloro-2,6-dimethylphenyl)-12-hydroxy-1,4-dioxa-9-azadispiro[4.2.4.2]tetradec-11-en-10-one, (28.29) 3-(4'-fluoro-2,4-dimethylbiphenyl-3-yl)-4-hydroxy-8-oxa-1-azaspiro[4.5]dec-3-en-2-one, and (28.30) 1-{2,4-dimethyl-5-[(2,2,2-trifluoroethyl)sulfinyl]phenyl}-3-(trifluoromethyl)-1H-1,2,4-triazole.

In a preferred embodiment this invention is directed to mixtures comprising the compound (I-1) as compound of formula (I) and one component (B), in particular the mixtures (I-1)+(1A.1), (I-1)+(1A.2), (I-1)+(1A.3), (I-1)+(1A.4), (I-1)+(1A.5), (I-1)+(1A.6), (I-1)+(1A.7), (I-1)+(1A.8), (I-1)+(1A.9), (I-1)+(1A.10), (I-1)+(1A.11), (I-1)+(1A.12), (I-1)+(1A.13), (I-1)+(1A.14), (I-1)+(1A.15), (I-1)+(1A.16), (I-1)+(1A.17), (I-1)+(1A.18), (I-1)+(1A.19), (I-1)+(1A.20), (I-1)+(1A.21), (I-1)+(1A.22), (I-1)+(1A.23), (I-1)+(1A.24), (I-1)+(1A.25), (I-1)+(1A.26), (I-1)+(1B.1), (I-1)+(1B.1), (I-1)+(1B.2), (I-1)+(1B.3), (I-1)+(1B.4), (I-1)+(1B.5), (I-1)+(1B.6), (I-1)+(1B.7), (I-1)+(1B.8), (I-1)+(1B.9), (I-1)+(1B.10), (I-1)+(1B.11), (I-1)+(1B.12), (I-1)+(1B.13), (I-1)+(1B.14), (I-1)+(1B.15), (I-1)+(1B.16), (I-1)+(1B.17), (I-1)+(1B.18), (I-1)+(1B.19), (I-1)+(1B.20), (I-1)+(1B.21), (I-1)+(1B.22), (I-1)+(1B.23), (I-1)+(1B.24), (I-1)+(1B.25), (I-1)+(1B.26), (I-1)+(1B.27), (I-1)+(1B.28), (I-1)+(1B.29), (I-1)+(1B.30), (I-1)+(1B.31), (I-1)+(1B.32), (I-1)+(1B.33), (I-1)+(1B.34), (I-1)+(1B.35), (I-1)+(1B.36), (I-1)+(1B.37), (I-1)+(1B.38), (I-1)+(1B.39), (I-1)+(1B.40), (I-1)+(1B.41), (I-1)+(1B.42), (I-1)+(1B.43), (I-1)+(1B.44), (I-1)+(1B.45), (I-1)+(1B.46), (I-1)+(1B.47), (I-1)+(1B.48), (I-1)+(1B.49), (I-1)+(1B.50), (I-1)±(1B.51), (I-1)+(1B.52), (I-1)+(1B.53), (I-1)+(1B.54), (I-1)+(1B.55), (I-1)+(1B.56), (I-1)+(1B.57), (I-1)+(1B.58), (I-1)+(1B.59), (I-1)+(1B.60), (I-1)+(1B.61), (I-1)+(1B.62), (I-1)+(1B.63), (I-1)+(1B.64), (I-1)+(1B.65), (I-1)+(1B.66), (I-1)+(2A.1), (I-1)+(2A.2), (I-1)+(2A.3), (I-1)+(2B.1), (I-1)+(2B.2), (I-1)+(2B.3), (I-1)+(2B.4), (I-1)+(3A.1), (I-1)+(3A.2), (I-1)+(3A.3), (I-1)+(3A.4), (I-1)+(3A.5), (I-1)+(3A.6), (I-1)+(3A.7), (I-1)+(3A.8), (I-1)+(3A.9), (I-1)+(3A.10), (I-1)+(3A.11), (I-1)+(3A.12), (I-1)+(3A.13), (I-1)+(3A.14), (I-1)+(3A.15), (I-1)+(3A.16), (I-1)+(3A.17), (I-1)+(3A.18), (I-1)+(3A.19), (I-1)+(3A.20), (I-1)+(3A.21), (I-1)+(3A.22), (I-1)+(3A.23), (I-1)+(3A.24), (I-1)+(3A.25), (I-1)+(3A.26), (I-1)+(3A.27), (I-1)+(3A.28), (I-1)+(3A.29), (I-1)+(3A.30), (I-1)+(3A.31), (I-1)+(3A.32), (I-1)+(3A.33), (I-1)+(3A.34), (I-1)+(3A.35), (I-1)+(3A.36), (I-1)+(3A.37), (I-1)+(3A.38), (I-1)+(3A.39), (I-1)+(3A.40), (I-1)+(3A.41), (I-1)+(3A.42), (I-1)+(3A.43), (I-1)+(3A.44), (I-1)+(3A.45), (I-1)+(3A.46), (I-1)+(3A.47), (I-1)+(3B.1), (I-1)+(3B.2), (I-1)+(4A.1), (I-1)+(4A.2), (I-1)+(4A.3), (I-1)+(4A.4), (I-1)+(4A.5), (I-1)+(4A.6), (I-1)+(4A.7), (I-1)+(4.B.1), (I-1)+(5.1), (I-1)+(5.2), (I-1)+(6.1), (I-1)+(6.2), (I-1)+(6.3), (I-1)+(6.4), (I-1)+(7.1), (I-1)+(7.2), (I-1)+(7.3), (I-1)+(7.4), (I-1)+(7.5), (I-1)+(8A.1), (I-1)+(8B.1), (I-1)+(8B.2), (I-1)+(8B.3), (I-1)+(8B.4), (I-1)+(9.1), (I-1)+(9.2), (I-1)+(10.1), (I-1)+(10.2), (I-1)+(10.3), (I-1)+(10.4), (I-1)+(11.1), (I-1)+(11.2), (I-1)+(11.3), (I-1)+(11.4), (I-1)+(11.5), (I-1)+(11.6), (I-1)+(11.7), (I-1)+(11.8), (I-1)+(11.9), (I-1)+(11.10), (I-1)+(11.11), (I-1)+(11.12), (I-1)+(11.13), (I-1)+(12A.1), (I-1)+(12B.1), (I-1)+(12B.2), (I-1)+(12B.3), (I-1)+(12C.1), (I-1)+(12C.2), (I-1)+(13.1), (I-1)+(13.2), (I-1)+(14.1), (I-1)+(14.2), (I-1)+(14.3), (I-1)+(14.4), (I-1)+(15.1), (I-1)+(15.2), (I-1)+(15.3), (I-1)+(15.4), (I-1)+(15.5), (I-1)+(15.6), (I-1)+(15.7), (I-1)+(15.8), (I-1)+(15.9), (I-1)+(15.10), (I-1)+(15.11), (I-1)+(15.12), (I-1)+(16.1), (I-1)+(17.1), (I-1)+(18.1), (I-1)+(18.2), (I-1)+(18.3), (I-1)+(18.4), (I-1)+(19.1), (I-1)+(20.1), (I-1)+(20.2), (I-1)+(20.3), (I-1)+(21.1), (I-1)+(21.2), (I-1)+(21.3), (I-1)+(21.4), (I-1)+(21.5), (I-1)+(21.6), (I-1)+(21.7), (I-1)+(22.1), (I-1)+(22.2), (I-1)+(23A.1), (I-1)+(23A.2), (I-1)+(23B.1), (I-1)+(24A.1), (I-1)+(24A.2), (I-1)+(24A.3), (I-1)+(24A.4), (I-1)+(23B.1), (I-1)+(25.1), (I-1)+(26.1), (I-1)+(26.2), (I-1)+(26.3), (I-1)+(27.1), (I-1)+(27.2), (I-1)+(27.3), (I-1)+(27.4), (I-1)+(27.5), (I-1)+(27.6), (I-1)+(27.7), (I-1)+(27.8), (I-1)+(27.9), (I-1)+(27.10), (I-1)+(27.11), (I-1)+(27.12), (I-1)+(27.13), (I-1)+(27.14), (I-1)+(27.15), (I-1)+(27.16), (I-1)+(27.17), (I-1)+(27.18), (I-1)+(27.19), (I-1)+(27.20), (I-1)+(27.21), (I-1)+(27.22), (I-1)+(27.23), (I-1)+(27.24), (I-1)+(27.25), (I-1)+(27.26), (I-1)+(27.27), (I-1)+(27.28), (I-1)+(28.29), (I-1)+(28.30).

In a further preferred embodiment this invention is directed to mixtures comprising the compound (I-1) as compound of formula (I) and one component (B), in particular the mixtures (I-1)+(1A.15), (I-1)+(1A.21), (I-1)+(2B.1), (I-1)+(2B.2), (I-1)+(3A.10), (I-1)+(3A.11), (I-1)+(3A.12), (I-1)+(3A.14), (I-1)+(3A.46), (I-1)+(4A.1), (I-1)+(4A.2), (I-1)+(4A.4), (I-1)+(4A.6), (I-1)+(4A.7), (I-1)+(5.1), (I-1)+(5.2), (I-1)+(6.1), (I-1)+(9.2), (I-1)+(27.15), (I-1)+(27.16), (I-1)+(27.27), (I-1)+(27.28), (I-1)+(28.29), (I-1)+(28.30).

In a preferred embodiment this invention is directed to mixtures comprising the compound (I-2) as compound of formula (I) and one component (B), in particular the mixtures (I-2)+(1A.1), (I-2)+(1A.2), (I-2)+(1A.3), (I-2)+(1A.4), (I-2)+(1A.5), (I-2)+(1A.6), (I-2)+(1A.7), (I-2)+(1A.8), (I-2)+(1A.9), (I-2)+(1A.10), (I-2)+(1A.11), (I-2)+(1A.12), (I-2)+(1A.13), (I-2)+(1A.14), (I-2)+(1A.15), (I-2)+(1A.16), (I-2)+(1A.17), (I-2)+(1A.18), (I-2)+(1A.19), (I-2)+(1A.20), (I-2)+(1A.21), (I-2)+(1A.22), (I-2)+(1A.23), (I-2)+(1A.24), (I-2)+(1A.25), (I-2)+(1A.26), (I-2)+(1B.1), (I-2)+(1B.1), (I-2)+(1B.2), (I-2)+(1B.3), (I-2)+(1B.4), (I-2)+(1B.5), (I-2)+(1B.6), (I-2)+(1B.7), (I-2)+(1B.8), (I-2)+(1B.9), (I-2)+(1B.10), (I-2)+(1B.11), (I-2)+(1B.12), (I-2)+(1B.13), (I-2)+(1B.14), (I-2)+(1B.15), (I-2)+(1B.16), (I-2)+(1B.17), (I-2)+(1B.18), (I-2)+(1B.19), (I-2)+(1B.20), (I-2)+(1B.21), (I-2)+(1B.22), (I-2)+(1B.23), (I-2)+(1B.24), (I-2)+(1B.25), (I-2)+(1B.26), (I-2)+(1B.27), (I-2)+(1B.28), (I-2)+(1B.29), (I-2)+(1B.30), (I-2)+(1B.31), (I-2)+(1B.32), (I-2)+(1B.33), (I-2)+(1B.34), (I-2)+(1B.35), (I-2)+(1B.36), (I-2)+(1B.37), (I-2)+(1B.38), (I-2)+(1B.39), (I-2)+(1B.40), (I-2)+(1B.41), (I-2)+(1B.42), (I-2)+(1B.43), (I-2)+(1B.44), (I-2)+(1B.45), (I-2)+(1B.46), (I-2)+(1B.47), (I-2)+(1B.48), (I-2)+(1B.49), (I-2)+(1B.50), (I-2)+(1B.51), (I-2)+(1B.52), (I-2)+(1B.53), (I-2)+(1B.54), (I-2)+(1B.55), (I-2)+(1B.56), (I-2)+(1B.57), (I-2)+(1B.58), (I-2)+(1B.59), (I-2)+(1B.60), (I-2)+(1B.61), (I-2)+(1B.62), (I-2)+(1B.63), (I-2)+(1B.64), (I-2)+(1B.65), (I-2)+(1B.66), (I-2)+(2A.1), (I-2)+(2A.2), (I-2)+(2A.3), (I-2)+(2B.1), (I-2)+(2B.2), (I-2)+(2B.3), (I-2)+(2B.4), (I-2)+(3A.1), (I-2)+(3A.2), (I-2)+(3A.3), (I-2)+(3A.4), (I-2)+(3A.5), (I-2)+(3A.6), (I-2)+(3A.7), (I-2)+(3A.8), (I-2)+(3A.9), (I-2)+(3A.10), (I-2)+(3A.11), (I-2)+(3A.12), (I-2)+(3A.13), (I-2)+(3A.14), (I-2)+(3A.15), (I-2)+(3A.16), (I-2)+(3A.17), (I-2)+(3A.18), (I-2)+(3A.19), (I-2)+(3A.20), (I-2)+(3A.21), (I-2)+(3A.22), (I-2)+(3A.23), (I-2)+(3A.24), (I-2)+(3A.25), (I-2)+(3A.26), (I-2)+(3A.27), (I-2)+(3A.28), (I-2)+(3A.29), (I-2)+(3A.30), (I-2)+(3A.31), (I-2)+(3A.32), (I-2)+(3A.33), (I-2)+(3A.34), (I-2)+(3A.35), (I-2)+(3A.36), (I-2)+(3A.37), (I-2)+(3A.38), (I-2)+(3A.39), (I-2)+(3A.40), (I-2)+(3A.41), (I-2)+(3A.42), (I-2)+(3A.43), (I-2)+(3A.44), (I-2)+(3A.45), (I-2)+(3A.46), (I-2)+(3A.47), (I-2)+(3B.1), (I-2)+(3B.2), (I-2)+(4A.1), (I-2)+(4A.2), (I-2)+(4A.3), (I-2)+(4A.4), (I-2)+(4A.5), (I-2)+(4A.6), (I-2)+(4A.7), (I-2)+

(4.B.1), (I-2)+(5.1), (I-2)+(5.2), (I-2)+(6.1), (I-2)+(6.2), (I-2)+(6.3), (I-2)+(6.4), (I-2)+(7.1), (I-2)+(7.2), (I-2)+(7.3), (I-2)+(7.4), (I-2)+(7.5), (I-2)+(8A.1), (I-2)+(8B.1), (I-2)+(8B.2), (I-2)+(8B.3), (I-2)+(8B.4), (I-2)+(9.1), (I-2)+(9.2), (I-2)+(10.1), (I-2)+(10.2), (I-2)+(10.3), (I-2)+(10.4), (I-2)+(11.1), (I-2)+(11.2), (I-2)+(11.3), (I-2)+(11.4), (I-2)+(11.5), (I-2)+(11.6), (I-2)+(11.7), (I-2)+(11.8), (I-2)+(11.9), (I-2)+(11.10), (I-2)+(11.11), (I-2)+(11.12), (I-2)+(11.13), (I-2)+(12A.1), (I-2)+(12B.1), (I-2)+(12B.2), (I-2)+(12B.3), (I-2)+(12C.1), (I-2)+(12C.2), (I-2)+(13.1), (I-2)+(13.2), (I-2)+(14.1), (I-2)+(14.2), (I-2)+(14.3), (I-2)+(14.4), (I-2)+(15.1), (I-2)+(15.2), (I-2)+(15.3), (I-2)+(15.4), (I-2)+(15.5), (I-2)+(15.6), (I-2)+(15.7), (I-2)+(15.8), (I-2)+(15.9), (I-2)+(15.10), (I-2)+(15.11), (I-2)+(15.12), (I-2)+(16.1), (I-2)+(17.1), (I-2)+(18.1), (I-2)+(18.2), (I-2)+(18.3), (I-2)+(18.4), (I-2)+(19.1), (I-2)+(20.1), (I-2)+(20.2), (I-2)+(20.3), (I-2)+(21.1), (I-2)+(21.2), (I-2)+(21.3), (I-2)+(21.4), (I-2)+(21.5), (I-2)+(21.6), (I-2)+(21.7), (I-2)+(22.1), (I-2)+(22.2), (I-2)+(23A.1), (I-2)+(23A.2), (I-2)+(23B.1), (I-2)+(24A.1), (I-2)+(24A.2), (I-2)+(24A.3), (I-2)+(24A.4), (I-2)+(23B.1), (I-2)+(25.1), (I-2)+(26.1), (I-2)+(26.2), (I-2)+(26.3), (I-2)+(27.1), (I-2)+(27.2), (I-2)+(27.3), (I-2)+(27.4), (I-2)+(27.5), (I-2)+(27.6), (I-2)+(27.7), (I-2)+(27.8), (I-2)+(27.9), (I-2)+(27.10), (I-2)+(27.11), (I-2)+(27.12), (I-2)+(27.13), (I-2)+(27.14), (I-2)+(27.15), (I-2)+(27.16), (I-2)+(27.17), (I-2)+(27.18), (I-2)+(27.19), (I-2)+(27.20), (I-2)+(27.21), (I-2)+(27.22), (I-2)+(27.23), (I-2)+(27.24), (I-2)+(27.25), (I-2)+(27.26), (I-2)+(27.27), (I-2)+(27.28), (I-2)+(28.29), (I-2)+(28.30).

In a further preferred embodiment this invention is directed to mixtures comprising the compound (I-2) as compound of formula (I) and one component (B), in particular the mixtures (I-2)+(1A.15), (I-2)+(1A.21), (I-2)+(2B.1), (I-2)+(2B.2), (I-2)+(3A.10), (I-2)+(3A.11), (I-2)+(3A.12), (I-2)+(3A.14), (I-2)+(3A.46), (I-2)+(4A.1), (I-2)+(4A.2), (I-2)+(4A.4), (I-2)+(4A.6), (I-2)+(4A.7), (I-2)+(5.1), (I-2)+(5.2), (I-2)+(6.1), (I-2)+(9.2), (I-2)+(27.15), (I-2)+(27.16), (I-2)+(27.27), (I-2)+(27.28), (I-2)+(28.29), (I-2)+(28.30).

In a preferred embodiment this invention is directed to mixtures comprising the compound (I-3) as compound of formula (I) and one component (B), in particular the mixtures (I-3)+(1A.1), (I-3)+(1A.2), (I-3)+(1A.3), (I-3)+(1A.4), (I-3)+(1A.5), (I-3)+(1A.6), (I-3)+(1A.7), (I-3)+(1A.8), (I-3)+(1A.9), (I-3)+(1A.10), (I-3)+(1A.11), (I-3)+(1A.12), (I-3)+(1A.13), (I-3)+(1A.14), (I-3)+(1A.15), (I-3)+(1A.16), (I-3)+(1A.17), (I-3)+(1A.18), (I-3)+(1A.19), (I-3)+(1A.20), (I-3)+(1A.21), (I-3)+(1A.22), (I-3)+(1A.23), (I-3)+(1A.24), (I-3)+(1A.25), (I-3)+(1A.26), (I-3)+(1B.1), (I-3)+(1B.1), (I-3)+(1B.2), (I-3)+(1B.3), (I-3)+(1B.4), (I-3)+(1B.5), (I-3)+(1B.6), (I-3)+(1B.7), (I-3)+(1B.8), (I-3)+(1B.9), (I-3)+(1B.10), (I-3)+(1B.11), (I-3)+(1B.12), (I-3)+(1B.13), (I-3)+(1B.14), (I-3)+(1B.15), (I-3)+(1B.16), (I-3)+(1B.17), (I-3)+(1B.18), (I-3)+(1B.19), (I-3)+(1B.20), (I-3)+(1B.21), (I-3)+(1B.22), (I-3)+(1B.23), (I-3)+(1B.24), (I-3)+(1B.25), (I-3)+(1B.26), (I-3)+(1B.27), (I-3)+(1B.28), (I-3)+(1B.29), (I-3)+(1B.30), (I-3)+(1B.31), (I-3)+(1B.32), (I-3)+(1B.33), (I-3)+(1B.34), (I-3)+(1B.35), (I-3)+(1B.36), (I-3)+(1B.37), (I-3)+(1B.38), (I-3)+(1B.39), (I-3)+(1B.40), (I-3)+(1B.41), (I-3)+(1B.42), (I-3)+(1B.43), (I-3)+(1B.44), (I-3)+(1B.45), (I-3)+(1B.46), (I-3)+(1B.47), (I-3)+(1B.48), (I-3)+(1B.49), (I-3)+(1B.50), (I-3)+(1B.51), (I-3)+(1B.52), (I-3)+(1B.53), (I-3)+(1B.54), (I-3)+(1B.55), (I-3)+(1B.56), (I-3)+(1B.57), (I-3)+(1B.58), (I-3)+(1B.59), (I-3)+(1B.60), (I-3)+(1B.61), (I-3)+(1B.62), (I-3)+(1B.63), (I-3)+(1B.64), (I-3)+(1B.65), (I-3)+(1B.66), (I-3)+(2A.1), (I-3)+(2A.2), (I-3)+(2A.3), (I-3)+(2B.1), (I-3)+(2B.2), (I-3)+(2B.3), (I-3)+(2B.4), (I-3)+(3A.1), (I-3)+(3A.2), (I-3)+(3A.3), (I-3)+(3A.4), (I-3)+(3A.5), (I-3)+(3A.6), (I-3)+(3A.7), (I-3)+(3A.8), (I-3)+(3A.9), (I-3)+(3A.10), (I-3)+(3A.11), (I-3)+(3A.12), (I-3)+(3A.13), (I-3)+(3A.14), (I-3)+(3A.15), (I-3)+(3A.16), (I-3)+(3A.17), (I-3)+(3A.18), (I-3)+(3A.19), (I-3)+(3A.20), (I-3)+(3A.21), (I-3)+(3A.22), (I-3)+(3A.23), (I-3)+(3A.24), (I-3)+(3A.25), (I-3)+(3A.26), (I-3)+(3A.27), (I-3)+(3A.28), (I-3)+(3A.29), (I-3)+(3A.30), (I-3)+(3A.31), (I-3)+(3A.32), (I-3)+(3A.33), (I-3)+(3A.34), (I-3)+(3A.35), (I-3)+(3A.36), (I-3)+(3A.37), (I-3)+(3A.38), (I-3)+(3A.39), (I-3)+(3A.40), (I-3)+(3A.41), (I-3)+(3A.42), (I-3)+(3A.43), (I-3)+(3A.44), (I-3)+(3A.45), (I-3)+(3A.46), (I-3)+(3A.47), (I-3)+(3B.1), (I-3)+(3B.2), (I-3)+(4A.1), (I-3)+(4A.2), (I-3)+(4A.3), (I-3)+(4A.4), (I-3)+(4A.5), (I-3)+(4A.6), (I-3)+(4A.7), (I-3)+(4.B.1), (I-3)+(5.1), (I-3)+(5.2), (I-3)+(6.1), (I-3)+(6.2), (I-3)+(6.3), (I-3)+(6.4), (I-3)+(7.1), (I-3)+(7.2), (I-3)+(7.3), (I-3)+(7.4), (I-3)+(7.5), (I-3)+(8A.1), (I-3)+(8B.1), (I-3)+(8B.2), (I-3)+(8B.3), (I-3)+(8B.4), (I-3)+(9.1), (I-3)+(9.2), (I-3)+(10.1), (I-3)+(10.2), (I-3)+(10.3), (I-3)+(10.4), (I-3)+(11.1), (I-3)+(11.2), (I-3)+(11.3), (I-3)+(11.4), (I-3)+(11.5), (I-3)+(11.6), (I-3)+(11.7), (I-3)+(11.8), (I-3)+(11.9), (I-3)+(11.10), (I-3)+(11.11), (I-3)+(11.12), (I-3)+(11.13), (I-3)+(12A.1), (I-3)+(12B.1), (I-3)+(12B.2), (I-3)+(12B.3), (I-3)+(12C.1), (I-3)+(12C.2), (I-3)+(13.1), (I-3)+(13.2), (I-3)+(14.1), (I-3)+(14.2), (I-3)+(14.3), (I-3)+(14.4), (I-3)+(15.1), (I-3)+(15.2), (I-3)+(15.3), (I-3)+(15.4), (I-3)+(15.5), (I-3)+(15.6), (I-3)+(15.7), (I-3)+(15.8), (I-3)+(15.9), (I-3)+(15.10), (I-3)+(15.11), (I-3)+(15.12), (I-3)+(16.1), (I-3)+(17.1), (I-3)+(18.1), (I-3)+(18.2), (I-3)+(18.3), (I-3)+(18.4), (I-3)+(19.1), (I-3)+(20.1), (I-3)+(20.2), (I-3)+(20.3), (I-3)+(21.1), (I-3)+(21.2), (I-3)+(21.3), (I-3)+(21.4), (I-3)+(21.5), (I-3)+(21.6), (I-3)+(21.7), (I-3)+(22.1), (I-3)+(22.2), (I-3)+(23A.1), (I-3)+(23A.2), (I-3)+(23B.1), (I-3)+(24A.1), (I-3)+(24A.2), (I-3)+(24A.3), (I-3)+(24A.4), (I-3)+(23B.1), (I-3)+(25.1), (I-3)+(26.1), (I-3)+(26.2), (I-3)+(26.3), (I-3)+(27.1), (I-3)+(27.2), (I-3)+(27.3), (I-3)+(27.4), (I-3)+(27.5), (I-3)+(27.6), (I-3)+(27.7), (I-3)+(27.8), (I-3)+(27.9), (I-3)+(27.10), (I-3)+(27.11), (I-3)+(27.12), (I-3)+(27.13), (I-3)+(27.14), (I-3)+(27.15), (I-3)+(27.16), (I-3)+(27.17), (I-3)+(27.18), (I-3)+(27.19), (I-3)+(27.20), (I-3)+(27.21), (I-3)+(27.22), (I-3)+(27.23), (I-3)+(27.24), (I-3)+(27.25), (I-3)+(27.26), (I-3)+(27.27), (I-3)+(27.28), (I-3)+(28.29), (I-3)+(28.30).

In a further preferred embodiment this invention is directed to mixtures comprising the compound (I-3) as compound of formula (I) and one component (B), in particular the mixtures (I-3)+(1A.15), (I-3)+(1A.21), (I-3)+(2B.1), (I-3)+(2B.2), (I-3)+(3A.10), (I-3)+(3A.11), (I-3)+(3A.12), (I-3)+(3A.14), (I-3)+(3A.46), (I-3)+(4A.1), (I-3)+(4A.2), (I-3)+(4A.4), (I-3)+(4A.6), (I-3)+(4A.7), (I-3)+(5.1), (I-3)+(5.2), (I-3)+(6.1), (I-3)+(9.2), (I-3)+(27.15), (I-3)+(27.16), (I-3)+(27.27), (I-3)+(27.28), (I-3)+(28.29), (I-3)+(28.30).

In a preferred embodiment this invention is directed to mixtures comprising the compound (I-4) as compound of formula (I) and one component (B), in particular the mixtures (I-4)+(1A.1), (I-4)+(1A.2), (I-4)+(1A.3), (I-4)+(1A.4), (I-4)+(1A.5), (I-4)+(1A.6), (I-4)+(1A.7), (I-4)+(1A.8), (I-4)+(1A.9), (I-4)+(1A.10), (I-4)+(1A.11), (I-4)+(1A.12), (I-4)+(1A.13), (I-4)+(1A.14), (I-4)+(1A.15), (I-4)+(1A.16), (I-4)+(1A.17), (I-4)+(1A.18), (I-4)+(1A.19), (I-4)+(1A.20), (I-4)+(1A.21), (I-4)+(1A.22), (I-4)+(1A.23), (I-4)+(1A.24), (I-4)+(1A.25), (I-4)+(1A.26), (I-4)+(1B.1), (I-4)+(1B.1), (I-4)+(1B.2), (I-4)+(1B.3), (I-4)+(1B.4), (I-4)+(1B.5), (I-4)+(1B.6), (I-4)+(1B.7), (I-4)+(1B.8), (I-4)+(1B.9), (I-4)+(1B.10), (I-4)+(1B.11), (I-4)+(1B.12), (I-4)+(1B.13), (I-4)+(1B.14), (I-4)+(1B.15), (I-4)+(1B.16), (I-4)+(1B.17), (I-4)+(1B.18), (I-4)+(1B.19), (I-4)+(1B.20), (I-4)+(1B.21), (I-4)+(1B.22), (I-4)+(1B.23), (I-4)+(1B.24), (I-4)+(1B.25), (I-4)+(1B.26), (I-4)+(1B.27), (I-4)+(1B.28), (I-4)+(1B.29), (I-4)+(1B.30), (I-4)+(1B.31), (I-4)+(1B.32), (I-4)+(1B.33), (I-4)+

(1B.34), (I-4)+(1B.35), (I-4)+(1B.36), (I-4)+(1B.37), (I-4)+ (1B.38), (I-4)+(1B.39), (I-4)+(1B.40), (I-4)+(1B.41), (I-4)+ (1B.42), (I-4)+(1B.43), (I-4)+(1B.44), (I-4)+(1B.45), (I-4)+ (1B.46), (I-4)+(1B.47), (I-4)+(1B.48), (I-4)+(1B.49), (I-4)+ (1B.50), (I-4)+(1B.51), (I-4)+(1B.52), (I-4)+(1B.53), (I-4)+ (1B.54), (I-4)+(1B.55), (I-4)+(1B.56), (I-4)+(1B.57), (I-4)+ (1B.58), (I-4)+(1B.59), (I-4)+(1B.60), (I-4)+(1B.61), (I-4)+ (1B.62), (I-4)+(1B.63), (I-4)+(1B.64), (I-4)+(1B.65), (I-4)+ (1B.66), (I-4)+(2A.1), (I-4)+(2A.2), (I-4)+(2A.3), (I-4)+ (2B.1), (I-4)+(2B.2), (I-4)+(2B.3), (I-4)+(2B.4), (I-4)+ (3A.1), (I-4)+(3A.2), (I-4)+(3A.3), (I-4)+(3A.4), (I-4)+ (3A.5), (I-4)+(3A.6), (I-4)+(3A.7), (I-4)+(3A.8), (I-4)+ (3A.9), (I-4)+(3A.10), (I-4)+(3A.11), (I-4)+(3A.12), (I-4)+ (3A.13), (I-4)+(3A.14), (I-4)+(3A.15), (I-4)+(3A.16), (I-4)+ (3A.17), (I-4)+(3A.18), (I-4)+(3A.19), (I-4)+(3A.20), (I-4)+ (3A.21), (I-4)+(3A.22), (I-4)+(3A.23), (I-4)+(3A.24), (I-4)+ (3A.25), (I-4)+(3A.26), (I-4)+(3A.27), (I-4)+(3A.28), (I-4)+ (3A.29), (I-4)+(3A.30), (I-4)+(3A.31), (I-4)+(3A.32), (I-4)+ (3A.33), (I-4)+(3A.34), (I-4)+(3A.35), (I-4)+(3A.36), (I-4)+ (3A.37), (I-4)+(3A.38), (I-4)+(3A.39), (I-4)+(3A.40), (I-4)+ (3A.41), (I-4)+(3A.42), (I-4)+(3A.43), (I-4)+(3A.44), (I-4)+ (3A.45), (I-4)+(3A.46), (I-4)+(3A.47), (I-4)+(3B.1), (I-4)+ (3B.2), (I-4)+(4A.1), (I-4)+(4A.2), (I-4)+(4A.3), (I-4)+ (4A.4), (I-4)+(4A.5), (I-4)+(4A.6), (I-4)+(4A.7), (I-4)+ (4.B.1), (I-4)+(5.1), (I-4)+(5.2), (I-4)+(6.1), (I-4)+(6.2), (I-4)+(6.3), (I-4)+(6.4), (I-4)+(7.1), (I-4)+(7.2), (I-4)+(7.3), (I-4)+(7.4), (I-4)+(7.5), (I-4)+(8A.1), (I-4)+(8B.1), (I-4)+ (8B.2), (I-4)+(8B.3), (I-4)+(8B.4), (I-4)+(9.1), (I-4)+(9.2), (I-4)+(10.1), (I-4)+(10.2), (I-4)+(10.3), (I-4)+(10.4), (I-4)+ (11.1), (I-4)+(11.2), (I-4)+(11.3), (I-4)+(11.4), (I-4)+(11.5), (I-4)+(11.6), (I-4)+(11.7), (I-4)+(11.8), (I-4)+(11.9), (I-4)+ (11.10), (I-4)+(11.11), (I-4)+(11.12), (I-4)+(11.13), (I-4)+ (12A.1), (I-4)+(12B.1), (I-4)+(12B.2), (I-4)+(12B.3), (I-4)+ (12C.1), (I-4)+(12C.2), (I-4)+(13.1), (I-4)+(13.2), (I-4)+ (14.1), (I-4)+(14.2), (I-4)+(14.3), (I-4)+(14.4), (I-4)+(15.1), (I-4)+(15.2), (I-4)+(15.3), (I-4)+(15.4), (I-4)+(15.5), (I-4)+ (15.6), (I-4)+(15.7), (I-4)+(15.8), (I-4)+(15.9), (I-4)+(15.10), (I-4)+(15.11), (I-4)+(15.12), (I-4)+(16.1), (I-4)+(17.1), (I-4)+(18.1), (I-4)+(18.2), (I-4)+(18.3), (I-4)+(18.4), (I-4)+ (19.1), (I-4)+(20.1), (I-4)+(20.2), (I-4)+(20.3), (I-4)+(21.1), (I-4)+(21.2), (I-4)+(21.3), (I-4)+(21.4), (I-4)+(21.5), (I-4)+ (21.6), (I-4)+(21.7), (I-4)+(22.1), (I-4)+(22.2), (I-4)+ (23A.1), (I-4)+(23A.2), (I-4)+(23B.1), (I-4)+(24A.1), (I-4)+ (24A.2), (I-4)+(24A.3), (I-4)+(24A.4), (I-4)+(23B.1), (I-4)+ (25.1), (I-4)+(26.1), (I-4)+(26.2), (I-4)+(26.3), (I-4)+(27.1), (I-4)+(27.2), (I-4)+(27.3), (I-4)+(27.4), (I-4)+(27.5), (I-4)+ (27.6), (I-4)+(27.7), (I-4)+(27.8), (I-4)+(27.9), (I-4)+(27.10), (I-4)+(27.11), (I-4)+(27.12), (I-4)+(27.13), (I-4)+(27.14), (I-4)+(27.15), (I-4)+(27.16), (I-4)+(27.17), (I-4)+(27.18), (I-4)+(27.19), (I-4)+(27.20), (I-4)+(27.21), (I-4)+(27.22), (I-4)+(27.23), (I-4)+(27.24), (I-4)+(27.25), (I-4)+(27.26), (I-4)+(27.27), (I-4)+(27.28), (I-4)+(28.29), (I-4)+(28.30).

In a further preferred embodiment this invention is directed to mixtures comprising the compound (I-4) as compound of formula (I) and one component (B), in particular the mixtures (I-4)+(1A.15), (I-4)+(1A.21), (I-4)+(2B.1), (I-4)+(2B.2), (I-4)+(3A.10), (I-4)+(3A.11), (I-4)+(3A.12), (I-4)+(3A.14), (I-4)+(3A.46), (I-4)+(4A.1), (I-4)+(4A.2), (I-4)+(4A.4), (I-4)+(4A.6), (I-4)+(4A.7), (I-4)+(5.1), (I-4)+(5.2), (I-4)+ (6.1), (I-4)+(9.2), (I-4)+(27.15), (I-4)+(27.16), (I-4)+(27.27), (I-4)+(27.28), (I-4)+(28.29), (I-4)+(28.30).

In a preferred embodiment this invention is directed to mixtures comprising the compound (I-5) as compound of formula (I) and one component (B), in particular the mixtures (I-5)+(1A.1), (I-5)+(1A.2), (I-5)+(1A.3), (I-5)+(1A.4), (I-5)+(1A.5), (I-5)+(1A.6), (I-5)+(1A.7), (I-5)+(1A.8), (I-5)+(1A.9), (I-5)+(1A.10), (I-5)+(1A.11), (I-5)+(1A.12), (I-5)+(1A.13), (I-5)+(1A.14), (I-5)+(1A.15), (I-5)+(1A.16), (I-5)+(1A.17), (I-5)+(1A.18), (I-5)+(1A.19), (I-5)+(1A.20), (I-5)+(1A.21), (I-5)+(1A.22), (I-5)+(1A.23), (I-5)+(1A.24), (I-5)+(1A.25), (I-5)+(1A.26), (I-5)+(1B.1), (I-5)+(1B.1), (I-5)+(1B.2), (I-5)+(1B.3), (I-5)+(1B.4), (I-5)+(1B.5), (I-5)+ (1B.6), (I-5)+(1B.7), (I-5)+(1B.8), (I-5)+(1B.9), (I-5)+ (1B.10), (I-5)+(1B.11), (I-5)+(1B.12), (I-5)+(1B.13), (I-5)+ (1B.14), (I-5)+(1B.15), (I-5)+(1B.16), (I-5)+(1B.17), (I-5)+ (1B.18), (I-5)+(1B.19), (I-5)+(1B.20), (I-5)+(1B.21), (I-5)+ (1B.22), (I-5)+(1B.23), (I-5)+(1B.24), (I-5)+(1B.25), (I-5)+ (1B.26), (I-5)+(1B.27), (I-5)+(1B.28), (I-5)+(1B.29), (I-5)+ (1B.30), (I-5)+(1B.31), (I-5)+(1B.32), (I-5)+(1B.33), (I-5)+ (1B.34), (I-5)+(1B.35), (I-5)+(1B.36), (I-5)+(1B.37), (I-5)+ (1B.38), (I-5)+(1B.39), (I-5)+(1B.40), (I-5)+(1B.41), (I-5)+ (1B.42), (I-5)+(1B.43), (I-5)+(1B.44), (I-5)+(1B.45), (I-5)+ (1B.46), (I-5)+(1B.47), (I-5)+(1B.48), (I-5)+(1B.49), (I-5)+ (1B.50), (I-5)+(1B.51), (I-5)+(1B.52), (I-5)+(1B.53), (I-5)+ (1B.54), (I-5)+(1B.55), (I-5)+(1B.56), (I-5)+(1B.57), (I-5)+ (1B.58), (I-5)+(1B.59), (I-5)+(1B.60), (I-5)+(1B.61), (I-5)+ (1B.62), (I-5)+(1B.63), (I-5)+(1B.64), (I-5)+(1B.65), (I-5)+ (1B.66), (I-5)+(2A.1), (I-5)+(2A.2), (I-5)+(2A.3), (I-5)+ (2B.1), (I-5)+(2B.2), (I-5)+(2B.3), (I-5)+(2B.4), (I-5)+ (3A.1), (I-5)+(3A.2), (I-5)+(3A.3), (I-5)+(3A.4), (I-5)+ (3A.5), (I-5)±(3A.6), (I-5)+(3A.7), (I-5)+(3A.8), (I-5)+ (3A.9), (I-5)+(3A.10), (I-5)+(3A.11), (I-5)+(3A.12), (I-5)+ (3A.13), (I-5)+(3A.14), (I-5)+(3A.15), (I-5)+(3A.16), (I-5)+ (3A.17), (I-5)+(3A.18), (I-5)+(3A.19), (I-5)+(3A.20), (I-5)+ (3A.21), (I-5)+(3A.22), (I-5)+(3A.23), (I-5)+(3A.24), (I-5)+ (3A.25), (I-5)+(3A.26), (I-5)+(3A.27), (I-5)+(3A.28), (I-5)+ (3A.29), (I-5)+(3A.30), (I-5)+(3A.31), (I-5)+(3A.32), (I-5)+ (3A.33), (I-5)+(3A.34), (I-5)+(3A.35), (I-5)+(3A.36), (I-5)+ (3A.37), (I-5)+(3A.38), (I-5)+(3A.39), (I-5)+(3A.40), (I-5)+ (3A.41), (I-5)+(3A.42), (I-5)+(3A.43), (I-5)+(3A.44), (I-5)+ (3A.45), (I-5)+(3A.46), (I-5)+(3A.47), (I-5)+(3B.1), (I-5)+ (3B.2), (I-5)+(4A.1), (I-5)+(4A.2), (I-5)+(4A.3), (I-5)+ (4A.4), (I-5)+(4A.5), (I-5)+(4A.6), (I-5)+(4A.7), (I-5)+ (4.B.1), (I-5)+(5.1), (I-5)+(5.2), (I-5)+(6.1), (I-5)+(6.2), (I-5)+(6.3), (I-5)+(6.4), (I-5)+(7.1), (I-5)+(7.2), (I-5)+(7.3), (I-5)+(7.4), (I-5)+(7.5), (I-5)+(8A.1), (I-5)+(8B.1), (I-5)+ (8B.2), (I-5)+(8B.3), (I-5)+(8B.4), (I-5)+(9.1), (I-5)+(9.2), (I-5)+(10.1), (I-5)+(10.2), (I-5)+(10.3), (I-5)+(10.4), (I-5)+ (11.1), (I-5)+(11.2), (I-5)+(11.3), (I-5)+(11.4), (I-5)+(11.5), (I-5)+(11.6), (I-5)+(11.7), (I-5)+(11.8), (I-5)+(11.9), (I-5)+ (11.10), (I-5)+(11.11), (I-5)+(11.12), (I-5)+(11.13), (I-5)+ (12A.1), (I-5)+(12B.1), (I-5)+(12B.2), (I-5)+(12B.3), (I-5)+ (12C.1), (I-5)+(12C.2), (I-5)+(13.1), (I-5)+(13.2), (I-5)+ (14.1), (I-5)+(14.2), (I-5)+(14.3), (I-5)+(14.4), (I-5)+(15.1), (I-5)+(15.2), (I-5)+(15.3), (I-5)+(15.4), (I-5)+(15.5), (I-5)+ (15.6), (I-5)+(15.7), (I-5)+(15.8), (I-5)+(15.9), (I-5)+(15.10), (I-5)+(15.11), (I-5)+(15.12), (I-5)+(16.1), (I-5)+(17.1), (I-5)+(18.1), (I-5)+(18.2), (I-5)+(18.3), (I-5)+(18.4), (I-5)+ (19.1), (I-5)+(20.1), (I-5)+(20.2), (I-5)+(20.3), (I-5)+(21.1), (I-5)+(21.2), (I-5)+(21.3), (I-5)+(21.4), (I-5)+(21.5), (I-5)+ (21.6), (I-5)+(21.7), (I-5)+(22.1), (I-5)+(22.2), (I-5)+ (23A.1), (I-5)+(23A.2), (I-5)+(23B.1), (I-5)+(24A.1), (I-5)+ (24A.2), (I-5)+(24A.3), (I-5)+(24A.4), (I-5)+(23B.1), (I-5)+ (25.1), (I-5)+(26.1), (I-5)+(26.2), (I-5)+(26.3), (I-5)+(27.1), (I-5)+(27.2), (I-5)+(27.3), (I-5)+(27.4), (I-5)+(27.5), (I-5)+ (27.6), (I-5)+(27.7), (I-5)+(27.8), (I-5)+(27.9), (I-5)+(27.10), (I-5)+(27.11), (I-5)+(27.12), (I-5)+(27.13), (I-5)+(27.14), (I-5)+(27.15), (I-5)+(27.16), (I-5)+(27.17), (I-5)+(27.18), (I-5)+(27.19), (I-5)+(27.20), (I-5)+(27.21), (I-5)+(27.22), (I-5)+(27.23), (I-5)+(27.24), (I-5)+(27.25), (I-5)+(27.26), (I-5)+(27.27), (I-5)+(27.28), (I-5)+(28.29), (I-5)+(28.30).

In a further preferred embodiment this invention is directed to mixtures comprising the compound (I-5) as compound of formula (I) and one component (B), in particular the mixtures (I-5)+(1A.15), (I-5)+(1A.21), (I-5)+(2B.1), (I-5)+(2B.2), (I-5)+(3A.10), (I-5)+(3A.11), (I-5)+(3A.12), (I-5)+(3A.14), (I-5)+(3A.46), (I-5)+(4A.1), (I-5)+(4A.2), (I-5)+(4A.4), (I-5)+(4A.6), (I-5)+(4A.7), (I-5)+(5.1), (I-5)+(5.2), (I-5)+(6.1), (I-5)+(9.2), (I-5)+(27.15), (I-5)+(27.16), (I-5)+(27.27), (I-5)+(27.28), (I-5)+(28.29), (I-5)+(28.30).

The active ingredients specified in this description by their "common name" are known, for example, from "The Pesticide Manual", 14$^{th}$ Edition, British Crop Protection Council 2006, and from the Web page http://www.alanwood.net/pesticides. In addition, compounds (27.12), (27.13, (27.14), (27.15), (27.16) are known from WO 2007/115644, compound (27.17) is known from WO 2007/115643, compound (27.18) is known from WO 2007/115646, compound (27.19) is known from WO 2007/115643, compounds (27.20) and (27.21) are known from EP-A 0 539 588, compounds (27.22), (27.23), (27.24), (27.25) and (27.27) are known from WO 2007/149134, compound (27.26) is known from WO 2007/095229, compound (27.28) is known from WO 2006/089633, compound (28.29) is known from WO 2008/067911, and compound (28.30) is known from WO 1999/55668.

If, in the context of this description, the short formi of the "common name" of an active compound is used, this comprises in each case all customary derivatives, such as the esters and salts, and isomers, in particular optical isomers, especially the commercially available form or fowls. If the "common name" refers to an ester or a salt, this in each case also comprises all other customary derivatives, such as other esters and salts, the free acids and neutral compounds, and isomers, in particular optical isomers, especially the commercially available form or forms. The given chemical compound names refer to at least one of the compounds embraced by the "common name", frequently to a preferred compound.

If the active compounds in the active compound combinations according to the invention are present in certain weight ratios, the synergistic effect is particularly pronounced. However, the weight ratios of the active compounds in the active compound combinations can be varied within a relatively wide range.

In the combinations according to the invention the compounds (A) and (B) are present in a synergistically effective weight ratio of A:B in a range of 250:1 to 1:250 or 125:1 to 1:125, preferably in a weight ratio of 50:1 to 1:50 or 25:1 to 1:25, most preferably in a weight ratio of 20:1 to 1:20 or 5:1 to 1:5. Further ratios of A:B which can be used according to the present invention with increasing preference in the order given are: 95:1 to 1:95, 90:1 to 1:90, 85:1 to 1:85, 80:1 to 1:80, 75:1 to 1:75, 70:1 to 1:70, 65:1 to 1:65, 60:1 to 1:60, 55:1 to 1:55, 45:1 to 1:45, 40:1 to 1:40, 35:1 to 1:35, 30:1 to 1:30, 25:1 to 1:25, 15:1 to 1:15, 10:1 to 1:10, 5:1 to 1:5, 4:1 to 1:4, 3:1 to 1:3, 2:1 to 1:2.

Where a compound (A) or a compound (B) can be present in tautomeric form, such a compound is understood hereinabove and hereinbelow also to include, where applicable, corresponding tautomeric forms, even when these are not specifically mentioned in each case.

Compounds (A) or compounds (B) having at least one basic centre are capable of forming, for example, acid addition salts, e.g. with strong inorganic acids, such as mineral acids, e.g. perchloric acid, sulfuric acid, nitric acid, nitrous acid, a phosphoric acid or a hydrohalic acid, with strong organic carboxylic acids, such as unsubstituted substituted, e.g. halo-substituted, $C_1$-$C_4$ alkanecarboxylic acids, e.g. acetic acid, saturated or unsaturated dicarboxylic acids, e.g. oxalic, malonic, succinic, maleic, fumaric and phthalic acid, hydroxycarboxylic acids, e.g. ascorbic, lactic, malic, tartaric and citric acid, or benzoic acid, or with organic sulfonic acids, such as unsubstituted or substituted, e.g. halo-substituted, $C_1$-$C_4$alkane- or aryl-sulfonic acids, e.g. methane- or p-toluene-sulfonic acid. Compounds (A) or compounds (B) having at least one acid group are capable of forming, for example, salts with bases, e.g. metal salts, such as alkali metal or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl-, diethyl-, triethyl- or dimethyl-propylamine, or a mono-, di- or tri-hydroxy-lower alkylamine, e.g. mono-, di- or tri-ethanolamine. In addition, corresponding internal salts may optionally be formed. In the context of the invention, preference is given to agrochemically advantageous salts. In view of the close relationship between the compounds (A) or the compounds (B) in free form and in the form of their salts, hereinabove and herein below any reference to the free compounds (A) or free compounds (B) or to their salts should be understood as including also the corresponding salts or the free compounds (A) or free compounds (B), respectively, where appropriate and expedient. The equivalent also applies to tautomers of compounds (A) or compounds (B) and to their salts.

According to the invention the expression "combination" stands for the various combinations of compounds (A) and (B), for example in a single "ready-mix" form, in a combined spray mixture composed from separate formulations of the single active compounds, such as a "tank-mix", and in a combined use of the single active ingredients when applied in a sequential manner, i.e. one after the other with a reasonably short period, such as a few hours or days. Preferably the order of applying the compounds (A) and (B) is not essential for working the present invention.

The present invention furthermore relates to compositions for combating/controlling undesirable microorganisms comprising the active compound combinations according to the invention. Preferably, the compositions are fungicidal compositions comprising agriculturally suitable auxiliaries, solvents, carriers, surfactants or extenders.

Furthermore the invention relates to a method of combating undesirable microorganisms, characterized in that the active compound combinations according to the invention are applied to the phytopathogenic fungi and/or their habitat.

The present invention furthermore relates to compositions for combating/controlling animal pests, preferably arthropods and nematodes, in particular insects and arachnids, encountered in viticulture, in the cultivation of fruit, in agriculture, in animal health, in forests, in the protection of stored products and in the protection of materials and also in the hygiene sector, said composition comprising the active compound combinations according to the invention. Preferably, the compositions are insecticidal and/or acaricidal compositions comprising agriculturally suitable auxiliaries, solvents, carriers, surfactants or extenders.

Furthermore the invention relates to a method of combating animal pests, characterized in that the active compound combinations according to the invention are applied to the animal pests and/or their habitat.

According to the invention, carrier is to be understood as meaning a natural or synthetic, organic or inorganic substance which is mixed or combined with the active compounds for better applicability, in particular for application to plants or plant parts or seeds. The carrier, which may be solid or liquid, is generally inert and should be suitable for use in agriculture.

Suitable solid or liquid carriers are: for example ammonium salts and natural ground minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral oils and vegetable oils, and also derivatives thereof. It is also possible to use mixtures of such carriers. Solid carriers suitable for granules are: for example crushed and fractionated natural minerals, such as calcite, marble, pumice, sepiolite, dolomite, and also synthetic granules of inorganic and organic meals and also granules of organic material, such as sawdust, coconut shells, maize cobs and tobacco stalks.

Suitable liquefied gaseous extenders or carriers are liquids which are gaseous at ambient temperature and under atmospheric pressure, for example aerosol propellants, such as butane, propane, nitrogen and carbon dioxide.

Tackifiers, such as carboxymethylcellulose and natural and synthetic polymers in the form of powders, granules and latices, such as gum arabic, polyvinyl alcohol, polyvinyl acetate, or else natural phospholipids, such as cephalins and lecithins and synthetic phospholipids can be used in the formulations. Other possible additives are mineral and vegetable oils and waxes, optionally modified.

If the extender used is water, it is also possible for example, to use organic solvents as auxiliary solvents. Suitable liquid solvents are essentially: aromatic compounds, such as xylene, toluene or alkylnaphthalenes, chlorinated aromatic compounds or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol, and also ethers and esters thereof, ketones, such as acetone, methyl ethyl ketone, methyl isobutyl ketone or cyclohexanone, strongly polar solvents, such as dimethylformamide and dimethyl sulphoxide, and also water.

The compositions according to the invention may comprise additional further components, such as, for example, surfactants. Suitable surfactants are emulsifiers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably allylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates. The presence of a surfactant is required if one of the active compounds and/or one of the inert carriers is insoluble in water and when the application takes place in water. The proportion of surfactants is between 5 and 40 percent by weight of the composition according to the invention.

It is possible to use colorants such as inorganic pigments, for example iron oxide, titanium oxide, Prussian blue, and organic dyes, such as alizarin dyes, azo dyes and metal phthalocyanine dyes, and trace nutrients, such as salts of iron, manganese, boron, copper, cobalt, molybdenum and zinc.

If appropriate, other additional components may also be present, for example protective colloids, binders, adhesives, thickeners, thixotropic substances, penetrants, stabilizers, sequestering agents, complex formers. In general, the active compounds can be combined with any solid or liquid additive customarily used for formulation purposes.

In general, the compositions according to the invention comprise between 0.05 and 99 percent by weight, 0.01 and 98 percent by weight, preferable between 0.1 and 95 percent by weight, particularly preferred between 0.5 and 90 percent by weight of the active compound combination according to the invention, very particularly preferable between 10 and 70 percent by weight.

The active compound combinations or compositions according to the invention can be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide-coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active compound, and also microencapsulations in polymeric substances and in coating materials for seed, and also ULV cold-fogging and warm-fogging formulations.

The formulations mentioned can be prepared in a manner known per se, for example by mixing the active compounds or the active compound combinations with at least one additive. Suitable additives are all customary formulation auxiliaries, such as, for example, organic solvents, extenders, solvents or diluents, solid carriers and fillers, surfactants (such as adjuvants, emulsifiers, dispersants, protective colloids, wetting agents and tackifiers), dispersants and/or binders or fixatives, preservatives, dyes and pigments, defoamers, inorganic and organic thickeners, water repellents, if appropriate siccatives and UV stabilizers, gibberellins and also water and further processing auxiliaries. Depending on the formulation type to be prepared in each case, further processing steps such as, for example, wet grinding, dry grinding or granulation may be required.

The compositions according to the invention do not only comprise ready-to-use compositions which can be applied with suitable apparatus to the plant or the seed, but also commercial concentrates which have to be diluted with water prior to use.

The active compound combinations according to the invention can be present in (commercial) formulations and in the use forms prepared from these foiniulations as a mixture with other (known) active compounds, such as insecticides, attractants, sterilants, bactericides, acaricides, nematicides, fungicides, growth regulators, herbicides, fertilizers, safeners and Semiochemicals.

The treatment according to the invention of the plants and plant parts with the active compounds or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more layers, etc. It is furthermore possible to apply the active compounds by the ultra-low volume method, or to inject the active compound preparation or the active compound itself into the soil.

The invention furthermore comprises a method for treating seed. The invention furthermore relates to seed treated according to one of the methods described in the preceding paragraph.

The active compounds or compositions according to the invention are especially suitable for treating seed. A large part of the damage to crop plants caused by harmful organisms is triggered by an infection of the seed during storage or after sowing as well as during and after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

The control of phytopathogenic fungi and/or animal pests by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with the additional application of crop protection agents after sowing or after the emergence of the plants or which at least considerably reduce additional application. It is furthermore desirable to optimize the amount of active compound employed in such a way as to provide maximum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

Accordingly, the present invention also relates in particular to a method for protecting seed and germinating plants against attack by phytopathogenic fungi and/or animal pests by treating the seed with a composition according to the invention. The invention also relates to the use of the compositions according to the invention for treating seed for protecting the seed and the germinating plant against phytopathogenic fungi and/or animal pests. Furthermore, the invention relates to seed treated with a composition according to the invention for protection against phytopathogenic fungi and/or animal pests.

The control of phytopathogenic fungi and/or animal pests which damage plants post-emergence is carried out primarily by treating the soil and the above-ground parts of plants with crop protection compositions. Owing to the concerns regarding a possible impact of the crop protection composition on the environment and the health of humans and animals, there are efforts to reduce the amount of active compounds applied.

One of the advantages of the present invention is that, because of the particular systemic properties of the compositions according to the invention, treatment of the seed with these compositions not only protects the seed itself, but also the resulting plants after emergence, from phytopathogenic fungi and/or animal pests. In this manner, the immediate treatment of the crop at the time of sowing or shortly thereafter can be dispensed with.

It is also considered to be advantageous that the mixtures according to the invention can be used in particular also for transgenic seed where the plant growing from this seed is capable of expressing a protein which acts against pests. By treating such seed with the active compound combinations or compositions according to the invention, even by the expression of the, for example, insecticidal protein, certain pests may be controlled. Surprisingly, a further synergistic effect may be observed here, which additionally increases the effectiveness of the protection against attack by pests.

The compositions according to the invention are suitable for protecting seed of any plant variety employed in agriculture, in the greenhouse, in forests or in horticulture or viticulture. In particular, this takes the form of seed of cereals (such as wheat, barley, rye, triticale, millet, oats), maize (corn), cotton, soya bean, rice, potatoes, sunflowers, beans, coffee, beets (e.g. sugar beets and fodder beets), peanuts, oilseed rape, poppies, olives, coconuts, cacao, sugar cane, tobacco, vegetables (such as tomatoes, cucumbers, onions and lettuce), lawn and ornamental plants (also see below). The treatment of seeds of cereals (such as wheat, barley, rye, triticale, and oats), maize (corn) and rice is of particular importance.

As also described further below, the treatment of transgenic seed with the active compound combinations or compositions according to the invention is of particular importance. This refers to the seed of plants containing at least one heterologous gene which allows the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. Preferably, this heterologous gene is from *Bacillus* sp., the gene product having activity against the European corn borer and/or the Western corn rootworm. Particularly preferably, the heterologous gene originates from *Bacillus thuringiensis*.

In the context of the present invention, the active compound combinations or compositions according to the invention are applied on their own or in a suitable formulation to the seed. Preferably, the seed is treated in a state in which it is sufficiently stable so that the treatment does not cause any damage. In general, treatment of the seed may take place at any point in time between harvesting and sowing. Usually, the seed used is separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which may have phytotoxic effects at certain application rates.

The compositions according to the invention can be applied directly, that is to say without comprising further components and without having been diluted. In general, it is preferable to apply the compositions to the seed in the form of a suitable formulation. Suitable formulations and methods for the treatment of seed are known to the person skilled in the art and are described, for example, in the following documents: U.S. Pat. Nos. 4,272,417 A, 4,245,432 A, 4,808,430 A, 5,876, 739 A, US 2003/0176428 A1, WO 2002/080675 A1, WO 2002/028186 A2.

The active compound combinations which can be used according to the invention can be converted into customary seed dressing formulations, such as solutions, emulsions, suspensions, powders, foams, slurries or other coating materials for seed, and also ULV formulations.

These formulations are prepared in a known manner by mixing the active compounds or active compound combinations with customary additives, such as, for example, customary extenders and also solvents or diluents, colorants, wetting agents, dispersants, emulsifiers, defoamers, preservatives, secondary thickeners, adhesives, gibberellins and water as well.

Suitable colorants that may be present in the seed dressing formulations which can be used according to the invention include all colorants customary for such purposes. Use may be made both of pigments, of sparing solubility in water, and of dyes, which are soluble in water. Examples that may be mentioned include the colorants known under the designations Rhodamine B, C.I. Pigment Red 112, and C.I. Solvent Red 1.

Suitable wetting agents that may be present in the seed dressing formulations which can be used according to the invention include all substances which promote wetting and are customary in the formulation of active agrochemical substances. With preference it is possible to use alkylnaphthalene-sulphonates, such as diisopropyl- or diisobutylnaphthalene-sulphonates.

Suitable dispersants and/or emulsifiers that may be present in the seed dressing formulations which can be used according to the invention include all nonionic, anionic, and cationic dispersants which are customary in the formulation of active agrochemical substances. With preference, it is possible to use nonionic or anionic dispersants or mixtures of nonionic or anionic dispersants. Particularly suitable nonionic dispersants are ethylene oxide-propylene oxide block polymers, alkylphenol polyglycol ethers, and tristyrylphenol polyglycol ethers, and their phosphated or sulphated derivatives. Particularly suitable anionic dispersants are lignosulphonates, polyacrylic salts, and arylsulphonate-formaldehyde condensates.

Defoamers that may be present in the seed dressing formulations to be used according to the invention include all foam-inhibiting compounds which are customary in the formulation of agrochemically active compounds. Preference is given to using silicone defoamers, magnesium stearate, silicone emulsions, long-chain alcohols, fatty acids and their salts and also organofluorine compounds and mixtures thereof. Preservatives that may be present in the seed dressing formulations to be used according to the invention include all compounds which can be used for such purposes in agrochemical compositions. By way of example, mention may be made of dichlorophen and benzyl alcohol hemiformal.

Secondary thickeners that may be present in the seed dressing formulations to be used according to the invention include all compounds which can be used for such purposes in agrochemical compositions. Preference is given to cellulose derivatives, acrylic acid derivatives, polysaccharides, such as xanthan gum or Veegum, modified clays, phyllosilicates, such as attapulgite and bentonite, and also finely divided silicic acids. Suitable adhesives that may be present in the seed dressing formulations to be used according to the invention include all customary binders which can be used in seed dressings. Polyvinylpyrrolidone, polyvinyl acetate, polyvinyl alcohol and tylose may be mentioned as being preferred.

Suitable gibberellins that may be present in the seed dressing formulations to be used according to the invention are preferably the gibberellins A1, A3 (=gibberellic acid), A4 and A7; particular preference is given to using gibberellic acid. The gibberellins are known (cf. R. Wegler "Chemie der Pflanzenschutz- and Schädlingsbekämpfungsmittel" [Chemistry of Crop Protection Agents and Pesticides], Vol. 2, Springer Verlag, 1970, pp. 401-412).

The seed dressing formulations which can be used according to the invention may be used directly or after dilution with water beforehand to treat seed of any of a very wide variety of types. The seed dressing formulations which can be used according to the invention or their dilute preparations may also be used to dress seed of transgenic plants. In this context, synergistic effects may also arise in interaction with the substances formed by expression.

Suitable mixing equipment for treating seed with the seed dressing formulations which can be used according to the invention or the preparations prepared from them by adding water includes all mixing equipment which can commonly be used for dressing. The specific procedure adopted when dressing comprises introducing the seed into a mixer, adding the particular desired amount of seed dressing formulation, either as it is or following dilution with water beforehand, and carrying out mixing until the formulation is unifoi oily distributed on the seed. Optionally, a drying operation follows.

The active compounds or compositions according to the invention have strong microbicidal activity and can be used for controlling unwanted microorganisms, such as fungi and bacteria, in crop protection and material protection.

In crop protection, fungicides can be used for controlling Plasmodiophoromycetes, Oomycetes, Chytridiomycetes, Zygomycetes, Ascomycetes, Basidiomycetes and Deuteromycetes.

In crop protection, bactericides can be used for controlling Pseudomonadaceae, Rhizobiaceae, Enterobacteriaceae, Corynebacteriaceae and Streptomycetaceae.

The fungicidal compositions according to the invention can be used for the curative or protective control of phytopathogenic fungi. Accordingly, the invention also relates to curative and protective methods for controlling phytopathogenic fungi using the active compound combinations or compositions according to the invention, which are applied to the seed, the plant or plant parts, the fruit or the soil in which the plants grow. Preference is given to application onto the plant or the plant parts, the fruits or the soil in which the plants grow.

The compositions according to the invention for combating phytopathogenic fungi in crop protection comprise an active, but non-phytotoxic amount of the compounds according to the invention. "Active, but non-phytotoxic amount" shall mean an amount of the composition according to the invention which is sufficient to control or to completely kill the plant disease caused by fungi, which amount at the same time does not exhibit noteworthy symptoms of phytotoxicity. These application rates generally may be varied in a broader range, which rate depends on several factors, e.g. the phytopathogenic fungi, the plant or crop, the climatic conditions and the ingredients of the composition according to the invention.

The fact that the active compounds, at the concentrations required for the controlling of plant diseases, are well tolerated by plants permits the treatment of aerial plant parts, of vegetative propagation material and seed, and of the soil.

According to the invention, it is possible to treat all plants and parts of plants. Plants are to be understood here as meaning all plants and plant populations, such as wanted and unwanted wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant variety protection rights. Parts of plants are to be understood as meaning all above-ground and below-ground parts and organs of the plants, such as shoot, leaf, flower and root, examples which may be mentioned being leaves, needles, stems, trunks, flowers, fruit bodies, fruits and seeds and also roots, tubers and rhizomes. Plant parts also include harvested material and vegetative and generative propagation material, for example seedlings, tubers, rhizomes, cuttings and seeds. Preference is given to the treatment of the plants and the above-ground and below-ground parts and organs of the plants, such as shoot, leaf, flower and root, examples which may be mentioned being leaves, needles, stems, trunks, flowers, and fruits.

The active compounds of the invention, in combination with good plant tolerance and favourable toxicity to warm-blooded animals and being tolerated well by the environment, are suitable for protecting plants and plant organs, for increasing the harvest yields, for improving the quality of the harvested material. They may be preferably employed as crop protection agents. They are active against normally sensitive and resistant species and against all or some stages of development.

The following plants may be mentioned as plants which can be treated according to the invention: cotton, flax, grapevines, fruit, vegetable, such as *Rosaceae* sp. (for example pomaceous fruit, such as apples and pears, but also stone fruit, such as apricots, cherries, almonds and peaches and soft fruit such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit), *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumbers), *Alliaceae* sp. (for example leek, onions), *Papilionaceae* sp. (for example peas); major crop plants, such *Gramineae* sp. (for example maize, lawn, cereals such as wheat, rye, rice, barley, oats, millet and triticale), *Asteraceae* sp. (for example sunflowers), *Brassicaceae* sp. (for example white cabbage, red cabbage, broccoli, cauliflowers, Brussels sprouts, pak choi, kohlrabi, garden radish, and also oilseed rape, mustard, horseradish and cress), *Fabacae* sp. (for example beans, peas, peanuts), *Papilionaceae* sp. (for example soya beans), *Solanaceae* sp. (for example potatoes), *Chenopodiaceae* sp. (for example sugar beet, fodder beet, Swiss chard, beetroot); crop plants and ornamental plants in garden and forest; and also in each case genetically modified varieties of these plants.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The terms "parts", "parts of plants" and "plant parts" have been explained above. Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

The method of treatment according to the invention is used in the treatment of genetically modified organisms (GMOs), e.g. plants or seeds. Genetically modified plants (or transgenic plants) are plants of which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by down regulating or silencing other gene(s) which are present in the plant (using for example, antisense technology, co-suppression technology or RNA interference—RNAi-technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in super-additive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted phytopathogenic fungi and/or microorganisms and/or viruses. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these phytopathogenic fungi and/or microorganisms and/or viruses, Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species. However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp, the genes encoding a Petunia EPSPS, a Tomato EPSPS, or an Eleusine EPSPS. It can also be a mutated EPSPS. Glyphosate-tolerant plants can also be obtained by expressing a gene that encodes a glyphosate oxido-reductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the above-mentioned genes.

Other herbicide resistant plants are for example plants that are made tolerant to herbicides inhibiting the enzyme glutamine synthase, such as bialaphos, phosphinothricin or glufosinate. Such plants can be obtamed by expressing an enzyme detoxifying the herbicide or a mutant glutamine synthase enzyme that is resistant to inhibition. One such efficient detoxifying enzyme is an enzyme encoding a phosphinothricin acetyltransferase (such as the bar or pat protein from *Streptomyces* species). Plants expressing an exogenous phosphinothricin acetyltransferase are also described.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme. Tolerance to HPPD-inhibitors can also be obtained by transforming plants with genes encoding certain enzymes enabling the formation of homogentisate despite the inhibition of the native HPPD enzyme by the HPPD-inhibitor. Tolerance of plants to HPPD inhibitors can also be improved by transforming plants with a gene encoding an enzyme prephenate dehydrogenase in addition to a gene encoding an HPPD-tolerant enzyme.

Still further herbicide resistant plants are plants that are made tolerant to acetolactate synthase (ALS) inhibitors. Known ALS-inhibitors include, for example, sulfonylurea, imidazolinone, triazolopyrimidines, pyrimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides. The production of sulfonylurea-tolerant plants and imidazolinone-tolerant plants is described in WO 1996/033270. Other imidazolinone-tolerant plants are also described. Further sulfonylurea- and imidazolinone-tolerant plants are also described in for example WO 2007/024782.

Other plants tolerant to imidazolinone and/or sulfonylurea can be obtained by induced mutagenesis, selection in cell cultures in the presence of the herbicide or mutation breeding as described for example for soybeans, for rice, for sugar beet, for lettuce, or for sunflower.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:
1) an insecticidal crystal protein from *Bacillus thuringiensis* or an insecticidal portion thereof, such as the insecticidal crystal proteins listed online at: http://www.lifesci.sussex.ac.uk/Home/Neil_Crickmore/Bt/, or insecticidal portions thereof, e.g., proteins of the Cry protein classes Cry1Ab, Cry1Ac, Cry1F, Cry2Ab, Cry3Aa, or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins; or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON98034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604;

5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g. proteins from the VIP3Aa protein class; or 6) secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins; or 7) hybrid insecticidal protein comprising parts from different secreted proteins from *Bacillus thuringiensis* or *Bacillus cereus*, such as a hybrid of the proteins in 1) above or a hybrid of the proteins in 2) above; or 8) protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102.

Of course, an insect-resistant transgenic plant, as used herein, also includes any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected when using different proteins directed at different target insect species, or to delay insect resistance development to the plants by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

a. plants which contain a transgene capable of reducing the expression and/or the activity of poly(ADP-ribose)polymerase (PARP) gene in the plant cells or plants b. plants which contain a stress tolerance enhancing transgene capable of reducing the expression and/or the activity of the PARG encoding genes of the plants or plants cells.

c. plants which contain a stress tolerance enhancing transgene coding for a plant-functional enzyme of the nicotinamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesised starch in wild type plant cells or plants, so that this is better suited for special applications.

2) transgenic plants which synthesize non starch carbohydrate polymers or which synthesize non starch carbohydrate polymers with altered properties in comparison to wild type plants without genetic modification. Examples are plants producing polyfructose, especially of the inulin and levan-type, plants producing alpha 1,4 glucans, plants producing alpha-1,6 branched alpha-1,4-glucans, plants producing alternan, 3) transgenic plants which produce hyaluronan.

Plants or plant cultivars (that can be obtained by plant biotechnology methods such as genetic engineering) which may also be treated according to the invention are plants, such as cotton plants, with altered fiber characteristics. Such plants can be obtained by genetic transformation or by selection of plants contain a mutation imparting such altered fiber characteristics and include:

a) Plants, such as cotton plants, containing an altered form of cellulose synthase genes, b) Plants, such as cotton plants, containing an altered form of rsw2 or rsw3 homologous nucleic acids, c) Plants, such as cotton plants, with increased expression of sucrose phosphate synthase, d) Plants, such as cotton plants, with increased expression of sucrose synthase, e) Plants, such as cotton plants, wherein the timing of the plasmodesmatal gating at the basis of the fiber cell is altered, e.g. through downregulation of fiberselective β 1,3-glucanase, f) Plants, such as cotton plants, having fibers with altered reactivity, e.g. through the expression of N-acteylglucosaminetransferase gene including nodC and chitinsynthase genes.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants contain a mutation imparting such altered oil characteristics and include:

a) Plants, such as oilseed rape plants, producing oil having a high oleic acid content,
b) Plants such as oilseed rape plants, producing oil having a low linolenic acid content,
c) Plant such as oilseed rape plants, producing oil having a low level of saturated fatty acids.

Particularly useful transgenic plants which may be treated according to the invention are plants which comprise one or more genes which encode one or more toxins, such as the following which are sold under the trade names YIELD GARD® (for example maize, cotton, soya beans), Knock-Out® (for example maize), BiteGard® (for example maize), Bt-Xtra® (for example maize), StarLink® (for example maize), Bollgard® (cotton), Nucotn® (cotton), Nucotn 33B® (cotton), NatureGard® (for example maize), Protecta® and New-Leaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oil-seed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or combination of transformation events, that are listed for example in the databases from various national or regional regulatory agencies (see for example http://gmoinfo.jrc.it/gmp_browse.aspx and http://www.agbios.com/dbase.php).

In material protection the substances of the invention may be used for the protection of technical materials against infestation and destruction by undesirable fungi and/or microorganisms.

Technical materials are understood to be in the present context non-living materials that have been prepared for use in engineering. For example, technical materials that are to be protected against microbiological change or destruction by the active materials of the invention can be adhesives, glues, paper and cardboard, textiles, carpets, leather, wood, paint and plastic articles, cooling lubricants and other materials that can be infested or destroyed by micro-organisms. Within the context of materials to be protected are also parts of production plants and buildings, for example cooling circuits, cooling and heating systems, air conditioning and ventilation systems, which can be adversely affected by the propagation of fungi and/or microorganisms. Within the context of the present invention, preferably mentioned as technical materials are adhesives, glues, paper and cardboard, leather, wood, paints, cooling lubricants and heat exchanger liquids, particularly preferred is wood. The combinations according to the invention can prevent disadvantageous effects like decaying, dis- and decoloring, or molding. The active compound combinations and compositions according to the invention can likewise be employed for protecting against colonization of objects, in particular ship hulls, sieves, nets, buildings, quays and signalling installations, which are in contact with sea water or brackish water.

The method of treatment according to the invention can also be used in the field of protecting storage goods against attack of fungi and microorganisms. According to the present invention, the term "storage goods" is understood to denote natural substances of vegetable or animal origin and their processed forms, which have been taken from the natural life cycle and for which long-term protection is desired. Storage goods of vegetable origin, such as plants or parts thereof, for example stalks, leafs, tubers, seeds, fruits or grains, can be protected in the freshly harvested state or in processed form, such as pre-dried, moistened, comminuted, ground, pressed or roasted. Also falling under the definition of storage goods is timber, whether in the form of crude timber, such as construction timber, electricity pylons and barriers, or in the form of finished articles, such as furniture or objects made from wood. Storage goods of animal origin are hides, leather, furs, hairs and the like. The combinations according the present invention can prevent disadvantageous effects such as decay, discoloration or mold. Preferably "storage goods" is understood to denote natural substances of vegetable origin and their processed foi ins, more preferably fruits and their processed forms, such as pomes, stone fruits, soft fruits and citrus fruits and their processed forms.

Some pathogens of fungal diseases which can be treated according to the invention may be mentioned by way of example, but not by way of limitation:

Diseases caused by powdery mildew pathogens, such as, for example, *Blumeria* species, such as, for example, *Blumeria graminis*; *Podosphaera* species, such as, for example, *Podosphaera leucotricha*; *Sphaerotheca* species, such as, for example, *Sphaerotheca fuliginea*; *Uncinula* species, such as, for example, *Uncinula necator*;

Diseases caused by rust disease pathogens, such as, for example, *Gymnosporangium* species, such as, for example, *Gymnosporangium sabinae*; *Hemileia* species, such as, for example, *Hemileia vastatrix*; *Phakopsora* species, such as, for example, *Phakopsora pachyrhizi* and *Phakopsora meibomiae*; *Puccinia* species, such as, for example, *Puccinia recondita* or *Puccinia triticina*; *Uromyces* species, such as, for example, *Uromyces appendiculatus*;

Diseases caused by pathogens from the group of the Oomycetes, such as, for example, *Bremia* species, such as, for example, *Bremia lactucae*; *Peronospora* species, such as, for example, *Peronospora pisi* or *P. brassicae*; *Phytophthora* species, such as, for example *Phytophthora infestans*; *Plasmopara* species, such as, for example, *Plasmopara viticola*; *Pseudoperonospora* species, such as, for example, *Pseudoperonospora humuli* or *Pseudoperonospora cubensis*; *Pythium* species, such as, for example, *Pythium ultimum*; Leaf blotch diseases and leaf wilt diseases caused, for example, by *Alternaria* species, such as, for example, *Alternaria solani*; *Cercospora* species, such as, for example, *Cercospora beticola*; *Cladiosporium* species, such as, for example, *Cladiosporium cucumerinum*; *Cochliobolus* species, such as, for example, *Cochliobolus sativus* (conidia form: *Drechslera*, Syn: *Helminthosporium*); *Colletotrichum* species, such as, for example, *Colletotrichum lindemuthanium*; *Cycloconium* species, such as, for example, *Cycloconium oleaginum*; *Diaporthe* species, such as, for example, *Diaporthe citri*; *Elsinoe* species, such as, for example, *Elsinoe fawcettii*; *Gloeosporium* species, such as, for example, *Gloeosporium laeticolor*; *Glomerella* species, such as, for example, *Glomerella cingulata*; *Guignardia* species, such as, for example, *Guignardia bidwelli*; *Leptosphaeria* species, such as, for example, *Leptosphaeria maculans*; *Magnaporthe* species, such as, for example, *Magnaporthe grisea*; *Microdochium* species, such as, for example, *Microdochium nivale*; *Mycosphaerella* species, such as, for example, *Mycosphaerella graminicola* and *M. fijiensis*; *Phaeosphaeria* species, such as, for example, *Phaeosphaeria nodorum*; *Pyrenophora* species, such as, for example, *Pyrenophora teres*; *Ramularia* species, such as, for example, *Ramularia collo-cygni*; *Rhynchosporium* species, such as, for example, *Rhynchosporium*

*secalis; Septoria* species, such as, for example, *Septoria apii; Typhula* species, such as, for example, *Typhula incamata; Venturia* species, such as, for example, *Venturia inaequalis;*

Root and stem diseases caused, for example, by *Corticium* species, such as, for example, *Corticium graminearum; Fusarium* species, such as, for example, *Fusarium oxysporum; Gaeumannomyces* species, such as, for example, *Gaeumannomyces graminis; Rhizoctonia* species, such as, for example *Rhizoctonia solani; Tapesia* species, such as, for example, *Tapesia acuformis; Thielaviopsis* species, such as, for example, *Thielaviopsis basicola;*

Ear and panicle diseases (including maize cobs) caused, for example, by *Alternaria* species, such as, for example, *Alternaria* spp.; *Aspergillus* species, such as, for example, *Aspergillus flavus; Cladosporium* species, such as, for example, *Cladosporium cladosporioides; Claviceps* species, such as, for example, *Claviceps purpurea; Fusarium* species, such as, for example, *Fusarium culmorum; Gibberella* species, such as, for example, *Gibberella zeae; Monographella* species, such as, for example, *Monographella nivalis; Septoria* species, such as for example, *Septoria nodorum;*

Diseases caused by smut fungi, such as, for example, *Sphacelotheca* species, such as, for example, *Sphacelotheca reiliana; Tilletia* species, such as, for example, *Tilletia caries; T. controversa; Urocystis* species, such as, for example, *Urocystis occulta; Ustilago* species, such as, for example, *Ustilago nuda; U. nuda tritici;*

Fruit rot caused, for example, by *Aspergillus* species, such as, for example, *Aspergillus flavus; Botrytis* species, such as, for example, *Botrytis cinerea; Penicillium* species, such as, for example, *Penicillium expansum* and *P. purpurogenum; Sclerotinia* species, such as, for example, *Sclerotinia sclerotiorum; Verticilium* species, such as, for example, *Verticilium alboatrum;*

Seed- and soil-borne rot and wilt diseases, and also diseases of seedlings, caused, for example, by *Fusarium* species, such as, for example, *Fusarium culmorum; Phytophthora* species, such as, for example, *Phytophthora cactorum; Pythium* species, such as, for example, *Pythium ultimum; Rhizoctonia* species, such as, for example, *Rhizoctonia solani; Sclerotium* species, such as, for example, *Sclerotium rolfsii;*

Cancerous diseases, galls and witches' broom caused, for example, by *Nectria* species, such as, for example, *Nectria galligena;*

Wilt diseases caused, for example, by *Monilinia* species, such as, for example, *Monilinia laxa;*

Deformations of leaves, flowers and fruits caused, for example, by *Taphrina* species, such as, for example, *Taphrina deformans;*

Degenerative diseases of woody plants caused, for example, by *Esca* species, such as, for example, *Phaemoniella clamydospora* and *Phaeoacremonium aleophilum* and *Fomitiporia mediterranea;*

Diseases of flowers and seeds caused, for example, by *Botrytis* species, such as, for example, *Botrytis cinerea;*

Diseases of plant tubers caused, for example, by *Rhizoctonia* species, such as, for example, *Rhizoctonia solani; Helminthosporium* species, such as, for example, *Helminthosporium solani;*

Diseases caused by bacteriopathogens, such as, for example, *Xanthomonas* species, such as, for example, *Xanthomonas campestris* pv. *oryzae; Pseudomonas* species, such as, for example, *Pseudomonas syringae* pv. *lachrymans; Erwinia* species, such as, for example, *Erwinia amylovora.*

Preference is given to controlling the following diseases of soya beans:

Fungal diseases on leaves, stems, pods and seeds caused, for example, by *alternaria* leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmopspora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia Southern blight (*Sclerotinia rolfsii*), thielaviopsis root rot (*Thielaviopsis basicola*).

It is also possible to control resistant strains of the organisms mentioned above.

Microorganisms capable of degrading or changing the industrial materials which may be mentioned are, for example, bacteria, fungi, yeasts, algae and slime organisms. The active compounds according to the invention preferably act against fungi, in particular moulds, wood-discolouring and wood-destroying fungi (Basidiomycetes) and against slime organisms and algae. Microorganisms of the following genera may be mentioned as examples: *Alternaria*, such as *Alternaria tenuis, Aspergillus*, such as *Aspergillus niger, Chaetomium*, such as *Chaetomium globosum, Coniophora*, such as *Coniophora puetana, Lentinus*, such as *Lentinus tigrinus, Penicillium*, such as *Penicillium glaucum, Polyporus*, such as *Polyporus versicolor, Aureobasidium*, such as *Aureobasidium pullulans, Sclerophoma*, such as *Sclerophoma pityophila, Trichoderma*, such as *Trichoderma viride, Escherichia*, such as *Escherichia coli, Pseudomonas*, such as *Pseudomonas aeruginosa*, and *Staphylococcus*, such as *Staphylococcus aureus*.

In addition, the compounds of the formula (I) according to the invention also have very good antimycotic activity. They have a very broad antimycotic activity spectrum in particular against dermatophytes and yeasts, moulds and diphasic fungi (for example against *Candida* species such as *Candida albicans, Candida glabrata*) and *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The list of these fungi by no means limits the mycotic spectrum which can be covered, but is only for illustration.

The active compounds of the invention are suitable for protecting plants and plant organs, for increasing harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They are active against normally sensitive and resistant species and against all or some stages of development. The abovementioned pests include:

From the phylum of Mollusca e.g. from the class of the Lamellibranchiata e.g. *Dreissena* spp.

From the class of the Gastropoda e.g. *Anion* spp., *Biomphalaria* spp., *Bulinus* spp., *Deroceras* spp., *Galba* spp., *Lymnaea* spp., *Oncomelania* spp., *Pomacea* spp., *Succinea* spp.

From the phylum: Arthropoda e.g. from the order of Isopoda e.g. *Armadillidium vulgare, Oniscus asellus, Porcellio scaber.*

From the class of the Arachnida e.g. *Acarus* spp., *Aceria sheldoni, Aculops* spp., *Aculus* spp., *Amblyomma* spp., *Amphitetranychus viennensis, Argas* spp., *Boophilus* spp., *Brevipalpus* spp., *Bryobia praetiosa, Centruroides* spp., *Chorioptes* spp., *Dermanyssus gallinae, Dermatophagoides pteronyssius, Dermatophagoides farinae, Dermacentor* spp., *Eotetranychus* spp., *Epitrimerus pyri, Eutetranychus* spp., *Eriophyes* spp., *Halotydeus destructor, Hemitarsonemus* spp., *Hyalomma* spp., *Ixodes* spp., *Latrodectus* spp., *Loxosceles* spp., *Metatetranychus* spp., *Nuphersa* spp., *Oligonychus* spp., *Ornithodorus* spp., *Ornithonyssus* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vaejovis* spp., *Vasates lycopersici.*

From the order of Symphyla e.g. *Scutigerella* spp.

From the order of Chilopoda e.g. *Geophilus* spp., *Scutigera* spp.

From the order of Collembola e.g. *Onychiurus armatus.*

From the order of Diplopoda e.g. *Blaniulus guttulatus.*

From the order of Zygentoma e.g. *Lepisma saccharina, Thermobia domestica.*

From the order of Orthoptera e.g. *Acheta domesticus, Blatta orientalis, Blattella germanica, Dichroplus* spp., *Gryllotalpa* spp., *Leucophaea maderae, Locusta* spp., *Melanoplus* spp., *Periplaneta* spp., *Pulex irritans, Schistocerca gregaria, Supella longipalpa.*

From the order of Isoptera e.g. *Coptotermes* spp., *Cornitermes cumulans, Cryptotermes* spp., *Incisitermes* spp., *Microtermes obesi, Odontotermes* spp., *Reticulitermes* spp., From the order of Heteroptera e.g. *Anasa tristis, Antestiopsis* spp., *Boisea* spp., *Blissus* spp., *Calocoris* spp., *Campylomma livida, Cavelerius* spp., *Cimex lectularius, Collaria* spp., *Creontiades dilutus, Dasynus piperic, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.

From the order of Anoplura (Phthiraptera) e.g. *Damalinia* spp., *Haematopinus* spp., *Linognathus* spp., *Pediculus* spp., *Ptirus pubis, Trichodectes* spp.

From the order of Homoptera e.g. *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

From the order of Coleoptera e.g. *Acalymma vittatum, Acanthoscelides obtectus, Adoretus* spp., *Agelastica alni, Agriotes* spp., *Alphitobius diaperinus, Amphimallon solstitialis, Anobium punctatum, Anoplophora* spp., *Anthonomus* spp., *Anthrenus* spp., *Apion* spp., *Apogonia* spp., *Atomaria* spp., *Attagenus* spp., *Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptorhynchus lapathi, Cylindrocopturus* spp., *Dennestes* spp., *Diabrotica* spp., *Dichocrocis* spp., *Diloboderus* spp., *Epilachna* spp., *Epitrix* spp., *Faustinus* spp., *Gibbium psylloides, Hellula undalis, Heteronychus arator, Heteronyx* spp., *Hylamorpha elegans, Hylotrupes bajulus, Hypera postica, Hypothenemus* spp., *Lachnostema consanguinea, Lema* spp., *Leptinotarsa decemlineata, Leucoptera* spp., *Lissorhoptrus oryzophilus, Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllotreta* spp., *Popillia japonica, Premnotrypes* spp., *Prostephanus truncatus, Psylliodes* spp., *Ptinus* spp., *Rhizobius ventralis, Rhizopertha dominica, Sitophilus* spp., *Sphenophorus* spp., *Stegobium paniceum, Stemechus* spp., *Symphyletes* spp., *Tanymecus* spp., *Tenebrio molitor, Tribolium* spp., *Trogoderma* spp., *Tychius* spp., *Xylotrechus* spp., *Zabrus* spp.

From the order of Hymenoptera e.g. *Acromyrmex* spp., *Athalia* spp., *Atta* spp., *Diprion* spp., *Hoplocampa* spp., *Lasius* spp., *Monomorium pharaonis, Solenopsis invicta, Tapinoma* spp., *Vespa* spp.

From the order of Lepidoptera e.g. *Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Chematobia brumata, Chilo* spp., *Choristoneura* spp., *Clysia ambiguella, Cnaphalocerus* spp., *Cnephasia* spp., *Conopomorpha* spp., *Conotrachelus* spp., *Copitarsia* spp., *Cydia* spp., *Dalaca noctuides, Diaphania* spp., *Diatraea saccharalis, Earias* spp., *Ecdytolopha aurantium, Elasmopalpus lignosellus, Eldana saccharina, Ephestia* spp., *Epinotia* spp., *Epiphyas postvittana, Etiella* spp., *Eulia* spp., *Eupoecilia ambiguella, Euproctis* spp., *Euxoa* spp., *Feltia* spp., *Galleria mellonella, Gracillaria* spp., *Grapholitha* spp., *Hedylepta* spp., *Helicoverpa* spp., *Heliothis* spp., *Holinannophila pseudospretella, Homoeosoma* spp., *Homona* spp., *Hyponomeuta padella, Kakivoria flavofasciata, Laphygma* spp., *Laspeyresia molesta, Leucinodes orbonalis, Leucoptera* spp, *Lithocolletis* spp., *Lithophane antermata, Lobesia* spp., *Loxagrotis albicosta, Lymantria* spp., *Lyonetia* spp., *Malacosoma neustria, Maruca testulalis, Mamestra brassicae, Mocis* spp., *Mythimna separata, Nymphula* spp., *Oiketicus* spp., *Oria* spp., *Orthaga* spp., *Ostrinia* spp., *Oulema oryzae, Panolis flammea, Parnara* spp., *Pectinophora* spp., *Perileucoptera* spp., *Phthorimaea* spp., *Phyllocnistis citrella, Phyllonorycter* spp., *Pieris* spp., *Platynota stultana, Plodia interpunctella, Plusia* spp., *Plutella xylostella, Prays* spp., *Prodenia* spp., *Protoparce* spp., *Pseudaletia* spp., *Pseudoplusia includens, Pyrausta nubilalis, Rachiplusia nu, Schoenobius* spp., *Scirpophaga* spp., *Scotia segetum, Sesamia* spp., *Sparganothis* spp., *Spodoptera* spp., *Stathmopoda* spp., *Stomopteryx subsecivella, Synanthedon* spp., *Tecia solanivora, Thermesia gemmatalis, Tinea pellionella, Tineola bisselliella, Tortrix* spp., *Trichophaga tapetzella, Trichoplusia* spp., *Tuta absoluta, Virachola* spp.

From the order of Diptera e.g. *Aedes* spp., *Agromyza* spp., *Anastrepha* spp., *Anopheles* spp., *Asphondylia* spp., *Bactrocera* spp., *Bibio hortulanus, Calliphora erythrocephala, Ceratitis capitata, Chironomus* spp., *Chrysomyia* spp., *Chrysops* spp., *Cochliomyia* spp., *Contarinia* spp., *Cordylobia anthropophaga, Culex* spp., *Culicoides* spp., *Culiseta* spp., *Cuterebra* spp., *Dacus oleae, Dasyneura* spp., *Delia* spp., *Dermatobia hominis, Drosophila* spp., *Echinocnemus* spp., *Fannia* spp., *Gasterophilus* spp., *Glossina* spp., *Haematopota* spp., *Hydrellia* spp., *Hylemyia* spp., *Hyppobosca* spp., *Hypoderma* spp., *Liriomyza* spp. *Lucilia* spp., *Lutzomia* spp., *Mansonia* spp., *Musca* spp., *Nezara* spp., *Oestrus* spp., *Oscinella frit, Pegomyia* spp., *Phlebotomus* spp., *Phorbia* spp., *Phormia* spp., *Prodiplosis* spp., *Psila rosae, Rhagoletis* spp., *Sarcophaga* spp., *Simulium* spp, *Stomoxys* spp., *Tabanus* spp., *Tannia* spp., *Tetanops* spp., *Tipula* spp.

From the order of Thysanoptera e.g. *Anaphothrips obscurus, Baliothrips biformis, Drepanothris reuteri, Enneothrips flavens, Frankliniella* spp., *Heliothrips* spp., *Hercinothrips femoralis, Rhipiphorothrips cruentatus, Scirtothrips* spp., *Taeniothrips cardamoni, Thrips* spp.

From the order of Siphonaptera e.g. *Ceratophyllus* spp., *Ctenocephalides* spp., *Tunga penetrans, Xenopsylla cheopis.*

From the phylums Plathelminthes and Nematoda as animal parasites e.g. from the class of the Helminths e.g. *Ancylostoma duodenale, Ancylostoma ceylanicum, Acylostoma braziliensis, Ancylostoma* spp., *Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., Loa Loa, *Nematodirus* spp., *Oesophagostomum* spp., *Opisthorchis* spp., *Onchocerca volvulus, Ostertagia* spp., *Paragonimus* spp., *Schistosomen* spp, *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

From the phylum Nematoda as plant pests e.e.g. *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis, Trichodorus* spp., *Tylenchulus semipenetrans, Xiphinema* spp.

From the subphylum of protozoa e.g. *Eimeria*.

When applying the compounds according to the invention the application rates can be varied within a broad range. The dose of active compound/application rate usually applied in the method of treatment according to the invention is generally and advantageously

- for treatment of aerial parts of plants, e.g. leaves, stems or shoots (foliar treatment): from 0.1 to 10,000 g/ha, preferably from 10 to 1,000 g/ha, more preferably from 50 to 300 g/ha; in case of drench or drip application, the dose can even be reduced, especially while using inert substrates like rockwool or perlite;
- for seed treatment: from 2 to 200 g per 100 kg of seed, preferably from 3 to 150 g per 100 kg of seed, more preferably from 2.5 to 25 g per 100 kg of seed, even more preferably from 2.5 to 12.5 g per 100 kg of seed;
- for soil treatment: from 0.1 to 10,000 g/ha, preferably from 1 to 5,000 g/ha.

The doses herein indicated are given as illustrative examples of the method according to the invention. A person skilled in the art will know how to adapt the application doses, notably according to the nature of the plant or crop to be treated.

The combination according to the invention can be used in order to protect plants within a certain time range after the treatment against pests and/or phytopathogenic fungi and/or microorganisms. The time range, in which protection is effected, spans in general 1 to 28 days, preferably 1 to 14 days, more preferably 1 to 10 days, even more preferably 1 to 7 days after the treatment of the plants with the combinations or up to 200 days after the treatment of plant propagation material.

Furthermore combinations and compositions according to the invention may also be used to reduce the contents of mycotoxins in plants and the harvested plant material and therefore in foods and animal feed stuff made therefrom. Especially but not exclusively the following mycotoxins can be specified: Deoxynivalenole (DON), Nivalenole, 15-Ac- DON, 3-Ac-DON, T2-und HT2-Toxins, Fumonisines, Zearalenone Moniliformine, Fusarine, Diaceotoxyscirpenole (DAS), Beauvericine, Enniatine, Fusaroproliferine, Fusarenole, Ochratoxines, Patuline, Ergotalkaloides und Aflatoxines, which are caused for example by the following fungal diseases: *Fusarium* spec., like *Fusarium acuminatum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides* and others but also by *Aspergillus* spec., *Penicillium* spec., *Claviceps purpurea, Stachybotrys* spec. and others.

The good fungicidal and/or insecticidal and/or acaricidal activity of the active compound combinations according to the invention is evident from the example below. While the individual active compounds exhibit weaknesses with regard to the fungicidal and/or insecticidal and/or acaricidal activity, the combinations have an activity which exceeds a simple addition of activities.

A synergistic effect of fungicides, insecticides and acaricides is always present when the fungicidal and/or insecticidal and/or acaricidal activity of the active compound combinations exceeds the total of the activities of the active compounds when applied individually.

The expected activity for a given combination of two active compounds can be calculated as follows (cf. Colby, S. R., "Calculating Synergistic and Antagonistic Responses of Herbicide Combinations", *Weeds* 1967, 15, 20-22):

If

X is the efficacy when active compound A is applied at an application rate of m ppm (or g/ha), Y is the efficacy when active compound B is applied at an application rate of n ppm (or g/ha), E is the efficacy when the active compounds A and B are applied at application rates of m and n ppm (or g/ha), respectively, and then $$E = X + Y - \frac{X \cdot Y}{100}$$

The degree of efficacy, expressed in % is denoted. 0% means an efficacy which corresponds to that of the control while an efficacy of 100% means that no disease is observed.

If the actual fungicidal activity exceeds the calculated value, then the activity of the combination is super-additive, i.e. a synergistic effect exists. In this case, the efficacy which was actually observed must be greater than the value for the expected efficacy (E) calculated from the abovementioned formula.

A further way of demonstrating a synergistic effect is the method of Tammes (cf. "Isoboles, a graphic representation of synergism in pesticides" in *Neth. J. Plant Path.*, 1964, 70, 73-80).

The invention is illustrated by the examples below. However, the invention is not limited to the examples.

USE EXAMPLES

Example A

*Myzus persicae* Test

| Solvent: | 7 parts by weight of dimethylformamide |
| Emulsifier: | 2 parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration. Cabbage leaves (*Brassica oleracea*) which are heavily infested by the Green peach aphid (*Myzus persicae*) are treated by being sprayed into the preparation of the active compound of the desired concentration. After the specified period of time, the mortality in % is determined. 100% means that all the aphids have been killed; 0% means that none of the aphids have been killed. In this test, for example, the following combinations according to the invention show a superior level of efficacy compared to the single compounds:

TABLE A

*Myzus persicae* test

| Active compounds | Concentration of active compound in ppm a.i. | Mortality in % after 4 h | |
| --- | --- | --- | --- |
| | | found* | calc.** |
| (I-1) 2,6-dimethyl-1H,5H-[1,4]dithiino[2,3-c:5,6-c']dipyrrole-1,3,5,7(2H,6H)-tetrone | 200 | 0 | |
| (4A.6) thiacloprid | 4 | 20 | |
| (I-1) + (4A.6) 50:1 | 200 + 4 | 40 | 20 |

| Active compounds | Concentration of active compound in ppm a.i. | Mortality in % after 1 d | |
| --- | --- | --- | --- |
| | | found* | calc.** |
| (I-1) 2,6-dimethyl-1H,5H-[1,4]dithiino[2,3-c:5,6-c']dipyrrole-1,3,5,7(2H,6H)-tetrone | 200 | 0 | |
| (4A.1) acetamiprid | 4 | 10 | |
| (27.27) sulfoxaflor | 0.8 | 20 | |
| (I-1) + (4A.1) 50:1 | 200 + 4 | 40 | 10 |
| (1-1) + (27.27) 250:1 | 200 + 0.8 | 50 | 20 |

TABLE A-continued

| | Myzus persicae test | | |
|---|---|---|---|
| | Concentration of active compound | Mortality in % after 2 d | |
| Active compounds | in ppm a.i. | found* | calc.** |
| (I-1) 2,6-dimethyl-1H,5H-[1,4]dithiino[2,3-c:5,6-c']dipyrrole-1,3,5,7(2H,6H)-tetrone | 200 | 0 | |
| (26.1) chloranthraniliprole | 0.8 | 40 | |
| (26.2) cyazypyr | 4 | 50 | |
| (I-1) + (26.1) 250:1 | 200 + 0.8 | 80 | 40 |
| (I-1) + (26.2) 50:1 | 200 + 4 | 70 | 50 |
| | Concentration of active compound | Mortality in % after 3 d | |
| Active compounds | in ppm a.i. | found* | calc.** |
| (I-1) 2,6-dimethyl-1H,5H-[1,4]dithiino[2,3-c:5,6-c']dipyrrole-1,3,5,7(2H,6H)-tetrone | 200 | 0 | |
| (3A.46) transfluthrin | 4 | 0 | |
| (I-1) + (3A.46) 50:1 | 200 + 4 | 20 | 0 |

*found = activity found
**calc. = activity calculated using Colby's formula

Example B

Phaedon cochleariae Larvae Test

| Solvent: | 7 parts by weight of dimethylformamide |
|---|---|
| Emulsifier: | 2 parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration. Cabbage leaves (Brassica oleracea) are treated by being sprayed into the preparation of the active compound of the desired concentration and are infested with larvae of the mustard beetle (Phaedon cochleariae) as long as the leaves are still moist. After the specified period of time, the mortality in % is determined. 100% means that all the beetle larvae have been killed; 0% means that none of the beetle larvae have been killed. In this test, for example, the following combinations according to the invention show a superior level of efficacy compared to the single compounds:

TABLE B

| | Phaedon cochleariae larvae test | | |
|---|---|---|---|
| | Concentration of active compound | Mortality in % after 1 d | |
| Active compounds | in ppm a.i. | found* | calc.** |
| (I-1) 2,6-dimethyl-1H,5H-[1,4]dithiino[2,3-c:5,6-c']dipyrrole-1,3,5,7(2H,6H)-tetrone | 200 | 0 | |
| (4A.4) imidacloprid | 20 | 0 | |
| (I-1) + (4A.4) 10:1 | 200 + 20 | 15 | 0 |
| | Concentration of active compound | Mortality in % after 3 d | |
| Active compounds | in ppm a.i. | found* | calc.** |
| (I-1) 2,6-dimethyl-1H,5H-[1,4]dithiino[2,3-c:5,6-c']dipyrrole-1,3,5,7(2H,6H)-tetrone | 200 | 0 | |
| (4A.1) acetamiprid | 4 | 0 | |
| (4A.2) clothianidin | 4 | 0 | |
| (26.2) cyazypyr | 0.8 | 25 | |
| (1A.15) methiocarb | 20 | 35 | |
| (I-1) + (4A.1) 50:1 | 200 + 4 | 30 | 0 |
| (I-1) + (4A.2) 50:1 | 200 + 4 | 25 | 0 |
| (I-1) + (26.2) 250:1 | 200 + 0.8 | 50 | 25 |
| (I-1) + (1A.15) 10:1 | 200 + 20 | 60 | 35 |

*found = activity found
**calc. = activity calculated using Colby's formula

Example C

*Plutella xylostella* Test

| | |
|---|---|
| Solvent: | 7 parts by weight of dimethylformamide |
| Emulsifier: | 2 parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration. Cabbage leaves (*Brassica oleracea*) are treated by being sprayed into the preparation of the active compound of the desired concentration and are infested with larvae of the diamondback moth (*Plutella xylostella*) as long as the leaves are still moist. After the specified period of time, the mortality in % is determined. 100% means that all the caterpillars have been killed; 0% means that none of the caterpillars have been killed. In this test, for example, the following combinations according to the invention show a superior level of efficacy compared to the single compounds:

TABLE C

*Plutella xylostella* test

| Active compounds | Concentration of active compound in ppm a.i. | Mortality in % after 1 d found* | calc.** |
|---|---|---|---|
| (I-1) 2,6-dimethyl-1H,5H-[1,4]dithiino[2,3-c:5,6-c']dipyrrole-1,3,5,7(2H,6H)-tetrone | 200 | 0 | |
| (6.1) abamectin | 4 | 75 | |
| (26.1) chloranthraniliprole | 4 | 25 | |
| (5.2) spinosad | 4 | 70 | |
| (I-1) + (6.1) 50:1 | 200 + 4 | 90 | 75 |
| (I-1) + (26.1) 50:1 | 200 + 4 | 45 | 25 |
| (I-1) + (5.2) 50:1 | 200 + 4 | 85 | 70 |

| Active compounds | Concentration of active compound in ppm a.i. | Mortality in % after 2 d found* | calc.** |
|---|---|---|---|
| (I-1) 2,6-dimethyl-1H,5H-[1,4]dithiino[2,3-c:5,6-c']dipyrrole-1,3,5,7(2H,6H)-tetrone | 200 | 0 | |
| (3A.11) β-cyfluthrin | 4 | 40 | |
| (I-1) + (3A.11) 10:1 | 200 + 4 | 65 | 40 |

*found = activity found
**calc. = activity calculated using Colby's formula

Example D

*Spodoptera frupperda* Test/Seed Application

Corn seeds were treated with a determined concentration of the active compounds. 14 days after sowing the leaves were cut off and infested with larvae of the fall army worm (*Spodoptera frugiperda*). After the specitied period of time, the mortality in % is determined. 100% means that all the caterpillars have been killed; 0% means that none of the caterpillars have been killed. In this test, for example, the following combinations according to the invention show a superior level of efficacy compared to the single compounds:

TABLE D

*Spodoptera frugiperda* test/seed application

| Active compounds | Concentration in mg a.i./seed | Efficacy in % 1 d after infestation found* | calc.** |
|---|---|---|---|
| (I-1) 2,6-dimethyl-1H,5H-[1,4]dithiino[2,3-c:5,6-c']dipyrrole-1,3,5,7(2H,6H)-tetrone | 1 | 0 | |
| (4 A.4) imidacloprid | 0.25 | 0 | |
| (I-1) + (4A.4) 4:1 | 1 + 0.25 | 28.6 | 0 |

TABLE D-continued

| | Spodoptera frugiperda test/seed application | | |
|---|---|---|---|
| | Concentration in mg | Efficacy in % 3 d after infestation | |
| Active compounds | a.i./seed | found* | calc.** |
| (I-1) 2,6-dimethyl-1H,5H-[1,4]dithiino[2,3-c:5,6-c']dipyrrole-1,3,5,7(2H,6H)-tetrone | 1 | 23.8 | |
| (6.1) abamectin | 0.25 | 4.8 | |
| (I-1) + (6.1) 4:1 | 1 + 0.25 | 38.1 | 27.5 |

*found = activity found
**calc. = activity calculated using Colby's formula

Example E

Alternaria Test (Tomatoes)/Preventive

| Solvent: | 24.5 parts by weight of acetone |
| --- | --- |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration. To test for preventive activity, young plants are sprayed with the preparation of active compound at the stated rate of application. After the spray coating has dried on, the plants are inoculated with an aqueous spore suspension of Alternaria solani. The plants are then placed in an incubation cabinet at approximately 20° C. and a relative atmospheric humidity of 100%. The test is evaluated 3 days after the inoculation. 0% means an efficacy which corresponds to that of the untreated control while an efficacy of 100% means that no disease is observed. The table below clearly shows that the observed activity of the active compound combination according to the invention is greater than the calculated activity, i.e. a synergistic effect is present.

TABLE E1

| | Alternaria test (tomatoes)/preventive | | |
|---|---|---|---|
| | Application rate of active compound | Efficacy in % | |
| Active compounds | in ppm a.i. | found* | calc.** |
| (I-1) 2,6-dimethyl-1H,5H-[1,4]dithiino[2,3-c:5,6-c']dipyrrole-1,3,5,7(2H,6H)-tetrone | 25 | 54 | |
| | 12.5 | 13 | |
| (4A.4) imidacloprid | 200 | 30 | |
| | 100 | 13 | |
| (4A.6) thiacloprid | 100 | 13 | |
| (4A.2) clothianidin | 200 | 45 | |
| | 100 | 49 | |
| (4A.7) thiamethoxam | 200 | 64 | |
| (26.1) chlorantraniliprole | 200 | 37 | |
| | 100 | 37 | |
| (26.2) cyantraniliprole | 100 | 28 | |
| (2B.2) fipronil | 200 | 44 | |
| | 100 | 28 | |
| (27.27) sulfoxaflor | 200 | 51 | |
| | 100 | 0 | |
| (I-1) + 4A.4) 1:8 | 25 + 200 | 92 | 68 |
| (I-1) + 4A.4) 1:4 | 25 + 100 | 70 | 60 |
| (I-1) + (4A.4) 1:16 | 12.5 + 200 | 84 | 39 |
| (I-1) + (4A.4) 1:8 | 12.5 + 100 | 71 | 24 |
| (I-1) + (4A.6) 1:4 | 25 + 100 | 83 | 60 |
| (I-1) + (4A.6) 1:8 | 12.5 + 100 | 67 | 24 |
| (I-1) + (4A.2) 1:8 | 25 + 200 | 91 | 75 |
| (I-1) + (4A.2) 1:16 | 12.5 + 200 | 93 | 52 |
| (I-1) + (4A.2) 1:8 | 12.5 + 100 | 69 | 56 |
| (I-1) + (4A.7) 1:16 | 12.5 + 200 | 91 | 78 |
| (I-1) + (26.1) 1:8 | 25 + 200 | 94 | 71 |
| (I-1) + (26.1) 1:4 | 25 + 100 | 84 | 71 |
| (I-1) + (26.1) 1:8 | 12.5 + 100 | 72 | 45 |
| (I-1) + (26.2) 1:8 | 12.5 + 100 | 68 | 37 |
| (I-1) + (2B.2) 1:8 | 25 + 200 | 88 | 74 |
| (I-1) + (2B.2) 1:4 | 25 + 100 | 77 | 67 |
| (I-1) + (2B.2) 1:8 | 12.5 + 100 | 57 | 37 |
| (I-1) + (27.27) 1:16 | 12.5 + 200 | 69 | 57 |
| (I-1) + (27.27) 1:4 | 25 + 100 | 77 | 54 |

*found = activity found
**calc. = activity calculated using Colby's formula

TABLE E2

| Active compounds | Application rate of active compound in ppm a.i. | Efficacy in % found* | Efficacy in % calc.** |
|---|---|---|---|
| (I-1) 2,6-dimethyl-1H,5H-[1,4]dithiino[2,3-c:5,6-c']dipyrrole-1,3,5,7(2H,6H)-tetrone | 50 | 58 | |
| | 25 | 50 | |
| | 12.5 | 30 | |
| (6.1) abamectin | 100 | 32 | |
| (1A.15) methiocarb | 200 | 47 | |
| | 100 | 45 | |
| (1A.21) thiodicarb | 200 | 52 | |
| (I-1) + (6.1) 1:8 | 12.5 + 100 | 69 | 52 |
| (I-1) + (1A.15) 1:16 | 12.5 + 200 | 84 | 63 |
| (I-1) + (1A.15) 1:2 | 50 + 100 | 87 | 77 |
| (I-1) + (1A.21) 1:8 | 25 + 200 | 89 | 76 |

*found = activity found
**calc. = activity calculated using Colby's formula

Example F

Botrytis Test (Beans)/Preventive

| Solvent: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration. To test for preventive activity, young plants are sprayed with the preparation of active compound. After the spray coating has dried on, 2 small pieces of agar covered with growth of Botrytis cinerea are placed on each leaf. The inoculated plants are placed in a darkened chamber at 20° C. and a relative atmospheric humidity of 100%. 2 days after the inoculation, the size of the lesions on the leaves is evaluated. 0% means an efficacy which corresponds to that of the untreated control, while an efficacy of 100% means that no disease is observed. The table below clearly shows that the observed activity of the active compound combination according to the invention is greater than the calculated activity, i.e. a synergistic effect is present.

TABLE F

| Active compounds | Application rate of active compound in ppm a.i. | Efficacy in % found* | Efficacy in % calc.** |
|---|---|---|---|
| (I-1) 2,6-dimethyl-1H,5H-[1,4]dithiino[2,3-c:5,6-c']dipyrrole-1,3,5,7(2H,6H)-tetrone | 50 | 48 | |
| | 25 | 13 | |
| (4A.1) acetamiprid | 100 | 0 | |
| (4A.7) thiamethoxam | 100 | 0 | |
| (26.1) chlorantraniliprole | 200 | 0 | |
| | 100 | 0 | |
| (26.2) cyantraniliprole | 200 | 0 | |
| | 100 | 0 | |
| (27.27) sulfoxaflor | 200 | 0 | |
| (I-1) + (4A.1) 1:2 | 50 + 100 | 63 | 48 |
| (I-1) + (4A.7) 1:2 | 50 + 100 | 68 | 48 |
| (I-1) + (26.1) 1:4 | 50 + 200 | 58 | 48 |
| (I-1) + (26.1) 1:2 | 50 + 100 | 85 | 48 |
| (I-1) + (26.1) 1:4 | 25 + 100 | 55 | 13 |
| (I-1) + (26.2) 1:4 | 50 + 200 | 66 | 48 |
| (I-1) + (26.2) 1:8 | 25 + 200 | 50 | 13 |
| (I-1) + (26.2) 1:2 | 50 + 100 | 83 | 48 |
| (I-1) + (27.27) 1:4 | 50 + 200 | 71 | 48 |
| (I-1) + (27.27) 1:8 | 25 + 200 | 50 | 13 |

*found = activity found
**calc. = activity calculated using Colby's formula

Example G

*Fusarium graminearum* Test (Barley)/Preventive

| Solvent: | 49 parts by weight of N,N-dimethylacetamid |
|---|---|
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration. To test for preventive activity, young plants are sprayed with the preparation of active compound or active compound combination at the stated rate of application. After the spray coating has been dried, the plants are slightly injured by using a sandblast and afterwards they are sprayed with a conidia suspension of *Fusarium graminearum*. The plants are placed in the greenhouse under a translucent incubation cabinet at a temperature of approximately 22° C. and a relative atmospheric humidity of approximately 100%. The test is evaluated 5 days after the inoculation. 0% means an efficacy which corresponds to that of the untreated control, while an efficacy of 100% means that no disease is observed. The table below clearly shows that the observed activity of the active compound combination according to the invention is greater than the calculated activity, i.e. a synergistic effect is present.

TABLE G

*Fusarium graminearum* test (barley)/preventive

| Active compounds | Application rate of active compound in ppm a.i. | Efficacy in % found* | calc.** |
|---|---|---|---|
| (I-1) 2,6-dimethyl-1H,5H-[1,4]dithiino[2,3-c:5,6-c']dipyrrole-1,3,5,7(2H,6H)-tetrone | 1000 | 50 | |
| (4A.4) imidacloprid | 1000 | 0 | |
| (I-1) + (4A.4) 1:1 | 1000 + 1000 | 67 | 50 |

*found = activity found
**calc. = activity calculated using Colby's formula

Example H

*Fusarium nivale* (var. *majus*)-Test (Wheat)/Preventive

| Solvent: | 49 parts by weight of N,N-dimethylacetamid |
|---|---|
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration. To test for preventive activity, young plants are sprayed with the preparation of active compound or active compound combination at the stated rate of application. After the spray coating has been dried, the plants are slightly injured by using a sandblast and afterwards they are sprayed with a conidia suspension of *Fusarium nivale* (var. *majus*). The plants are placed in the greenhouse under a translucent incubation cabinet at a temperature of approximately 10° C. and a relative atmospheric humidity of approximately 100%. The test is evaluated 5 days after the inoculation. 0% means an efficacy which corresponds to that of the untreated control, while an efficacy of 100% means that no disease is observed. The table below clearly shows that the observed activity of the active compound combination according to the invention is greater than the calculated activity, i.e. a synergistic effect is present.

TABLE H

| | Fusarium nivale (var. majus)-test (wheat)/preventive | | |
|---|---|---|---|
| Active compounds | Application rate of active compound in ppm a.i. | Efficacy in % found* | calc.** |
| (I-1) 2,6-dimethyl-1H,5H-[1,4]dithiino[2,3-c:5,6-c']dipyrrole-1,3,5,7(2H,6H)-tetrone | 500 | 29 | |
| (4A.6) thiacloprid | 1000 | 0 | |
| (1A.21) thiodicarb | 1000 | 0 | |
| (I-1) + (4A.6) 1:2 | 500 + 1000 | 71 | 29 |
| (I-1) + (1A.21) 1:2 | 500 + 1000 | 57 | 29 |

*found = activity found
**calc. = activity calculated using Colby's formula

Example I

Phytophthora Test (Tomatoes)/Preventive

| Solvent: | 24.5 parts by weight of acetone |
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration. To test for preventive activity, young plants are sprayed with the preparation of active compound at the stated rate of application. After the spray coating has dried on, the plants are inoculated with an aqueous spore suspension of Phytophthora infestans. The plants are then placed in an incubation cabinet at approximately 20° C. and a relative atmospheric humidity of 100%. The test is evaluated 3 days after the inoculation. 0% means an efficacy which corresponds to that of the untreated control, while an efficacy of 100% means that no disease is observed. The table below clearly shows that the observed activity of the active compound combination according to the invention is greater than the calculated activity, i.e. a synergistic effect is present.

TABLE I1

| | Phytophthora test (tomatoes)/preventive | | |
|---|---|---|---|
| Active compounds | Application rate of active compound in ppm a.i. | Efficacy in % found* | calc.** |
| (I-1) 2,6-dimethyl-1H,5H-[1,4]dithiino[2,3-c:5,6-c']dipyrrole-1,3,5,7(2H,6H)-tetrone | 50 | 43 | |
| | 12.5 | 18 | |
| 4A.1 acetamiprid | 200 | 27 | |
| 4A.6 thiacloprid | 100 | 16 | |
| 4A.2 clothianidin | 100 | 30 | |
| 4A.7 thiamethoxam | 100 | 30 | |
| 26.1 chlorantraniliprole | 100 | 32 | |
| 26.2 cyantraniliprole | 100 | 30 | |
| 2B.2 fipronil | 200 | 47 | |
| | 100 | 30 | |
| (I-1) + 4A.1 1:4 | 50 + 200 | 86 | 58 |
| (I-1) + 4A.6 1:2 | 50 + 100 | 82 | 52 |
| (I-1) + 4A.6 1:8 | 12.5 + 100 | 58 | 31 |
| (I-1) + 4A.2 1:2 | 50 + 100 | 80 | 60 |
| (I-1) + 4A.7 1:2 | 50 + 100 | 82 | 60 |
| (I-1) + 26.1 1:2 | 50 + 100 | 73 | 61 |
| (I-1) + 26.1 1:8 | 12.5 + 100 | 59 | 44 |
| (I-1) + 26.2 1:2 | 50 + 100 | 84 | 60 |
| (I-1) + 2B.2 1:4 | 50 + 200 | 90 | 70 |
| (I-1) + 2B.2 1:16 | 12.5 + 200 | 71 | 57 |
| (I-1) + 2B.2 1:2 | 50 + 100 | 85 | 60 |
| (I-1) + 2B.2 1:8 | 12.5 + 100 | 55 | 43 |

*found = activity found
**calc. = activity calculated using Colby's formula

TABLE I2

Phytophthora test (tomatoes)/preventive

| Active compounds | Application rate of active compound in ppm a.i. | Efficacy in % found* | Efficacy in % calc.** |
|---|---|---|---|
| (I-1) 2,6-dimethyl-1H,5H-[1,4]dithiino[2,3-c:5,6-c']dipyrrole-1,3,5,7(2H,6H)-tetrone | 50 | 28 | |
| (2A.43) tefluthrin | 200 | 0 | |
| (5.2) spinosad | 100 | 10 | |
| (1A.15) methiocarb | 100 | 16 | |
| (27.16) 4-{[(6-chloropyridin-3-yl)methyl](2,2-difluoroethyl)amino}furan-2(5H)-one | 200 | 30 | |
| (I-1) + (2A.43) 1:4 | 50 + 200 | 55 | 28 |
| (I-1) + (5.2) 1:2 | 50 + 100 | 50 | 35 |
| (I-1) + (1A.15) 1:2 | 50 + 100 | 56 | 40 |
| (I-1) + (27.16) 1:4 | 50 + 200 | 60 | 50 |

*found = activity found
**calc. = activity calculated using Colby's formula

Example J

Pyrenophora teres Test (Barley)/Preventive

| | |
|---|---|
| Solvent: | 49 parts by weight of N,N-dimethylacetamid |
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration. To test for preventive activity, young plants are sprayed with the preparation of active compound or active compound combination at the stated rate of application. After the spray coating has been dried, the plants are sprayed with a spore suspension of Pyrenophora teres. The plants remain for 48 hours in an incubation cabinet at approximately 20° C. and a relative atmospheric humidity of approximately 100%. The plants are placed in the greenhouse at a temperature of approximately 20° C. and a relative atmospheric humidity of approximately 80%. The test is evaluated 8 days after the inoculation. 0% means an efficacy which corresponds to that of the untreated control, while an efficacy of 100% means that no disease is observed. The table below clearly shows that the observed activity of the active compound combination according to the invention is greater than the calculated activity, i.e. a synergistic effect is present.

TABLE J1

Pyrenophora teres test (barley)/preventive

| Active compounds | Application rate of active compound in ppm a.i. | Efficacy in % found* | Efficacy in % calc.** |
|---|---|---|---|
| (I-1) 2,6-dimethyl-1H,5H-[1,4]dithiino[2,3-c:5,6-c']dipyrrole-1,3,5,7(2H,6H)-tetrone | 1000 | 43 | |
| (4A.7) thiamethoxam | 1000 | 0 | |
| (5.2) spinosad | 1000 | 0 | |
| (I-1) + (4A.7) 1:1 | 1000 + 1000 | 86 | 43 |
| (I-1) + (5.2) 1:1 | 1000 + 1000 | 93 | 43 |

*found = activity found
**calc. = activity calculated using Colby's formula

TABLE J2

Pyrenophora teres test (barley)/preventive

| Active compounds | Application rate of active compound in ppm a.i. | Efficacy in % found* | Efficacy in % calc.** |
|---|---|---|---|
| (I-1) 2,6-dimethyl-1H,5H-[1,4]dithiino[2,3-c:5,6-c']dipyrrole-1,3,5,7(2H,6H)-tetrone | 500 | 43 | |
| (2B.2) fipronil | 500 | 0 | |
| (3A.10) cyfluthrin | 500 | 0 | |
| (26.1) chlorantraniliprole | 500 | 14 | |
| (4A.2) clothianidin | 500 | 0 | |

TABLE J2-continued

*Pyrenophora teres* test (barley)/preventive

| Active compounds | Application rate of active compound in ppm a.i. | Efficacy in % found* | calc.** |
|---|---|---|---|
| (I-1) + (2B.2) 1:1 | 500 + 500 | 57 | 43 |
| (I-1) + (3A.10) 1:1 | 500 + 500 | 57 | 43 |
| (I-1) + (26.1) 1:1 | 500 + 500 | 71 | 51 |
| (I-1) + (4A.2) 1:1 | 500 + 500 | 57 | 43 |

*found = activity found
**calc. = activity calculated using Colby's formula

Example K

*Septoria tritici* Test (Wheat)/Preventive

| Solvent: | 49 parts by weight of n,n-dimethylacetamid |
|---|---|
| Emulsifier: | 1 part by weight of alkylaryl polyglycol ether |

To produce a suitable preparation of active compound, 1 part by weight of active compound or active compound combination is mixed with the stated amounts of solvent and emulsifier, and the concentrate is diluted with water to the desired concentration. To test for preventive activity, young plants are sprayed with the preparation of active compound or active compound combination at the stated rate of application. After the spray coating has been dried, the plants are sprayed with a spore suspension of *Septoria tritici*. The plants remain for 48 hours in an incubation cabinet at approximately 20° C. and a relative atmospheric humidity of approximately 100% and afterwards for 60 hours at approximately 15° C. in a translucent incubation cabinet at a relative atmospheric humidity of approximately 100%. The plants are placed in the greenhouse at a temperature of approximately 15° C. and a relative atmospheric humidity of approximately 80%. The test is evaluated 21 days after the inoculation. 0% means an efficacy which corresponds to that of the untreated control, while an efficacy of 100% means that no disease is observed. The table below clearly shows that the observed activity of the active compound combination according to the invention is greater than the calculated activity, i.e. a synergistic effect is present.

TABLE K

*Septoria tritici* test (wheat)/preventive

| Active compounds | Application rate of active compound in ppm a.i. | Efficacy in % found* | calc.** |
|---|---|---|---|
| (I-1) 2,6-dimethyl-1H,5H-[1,4]dithiino[2,3-c:5,6-c']dipyrrole-1,3,5,7(2H,6H)-tetrone | 500 | 0 | |
| (3A.43) tefluthrin | 500 | 0 | |
| (27.16) 4-{[(6-chloropyridin-3-yl)methyl](2,2-difluoroethyl)amino}furan-2(5H)-one | 1000 | 0 | |
| (I-1) + (3A.43) 1:1 | 500 + 500 | 56 | 0 |
| (I-1) + (27.16) 1:2 | 500 + 1000 | 56 | 0 |

*found = activity found
**calc. = activity calculated using Colby's formula

Example L

*Venturia* Test (Apples)/Preventive

| Solvent: | 24.5 parts by weight of acetone |
|---|---|
| | 24.5 parts by weight of dimethylacetamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration. To test for preventive activity, young plants are sprayed with the preparation of active compound at the stated rate of application. After the spray coating has dried on, the plants are inoculated with an aqueous conidia suspension of the causal agent of apple scab (*Venturia inaequalis*) and then remain for 1 day in an incubation cabinet at approximately 20° C. and a relative atmospheric humidity of 100%. The plants are then placed in a greenhouse at approximately 21° C. and a relative atmospheric humidity of approximately 90%. The test is evaluated 10 days after the inoculation. 0% means an efficacy which corresponds to that of the untreated control, while an efficacy of 100% means that no disease is observed. The table below clearly shows that the observed activity of the active compound combination according to the invention is greater than the calculated activity, i.e. a synergistic effect is present.

TABLE L1

Venturia test (apples)/preventive

| Active compounds | Application rate of active compound in ppm a.i. | Efficacy in % found* | calc.** |
|---|---|---|---|
| (I-1) 2,6-dimethyl-1H,5H-[1,4]dithiino[2,3-c:5,6-c']dipyrrole-1,3,5,7(2H,6H)-tetrone | 50 | 29 | |
| (4A.6) thiacloprid | 200 | 4 | |
| (4A.2) clothianidin | 200 | 0 | |
| | 100 | 0 | |
| (4A.7) thiamethoxam | 200 | 25 | |
| | 100 | 18 | |
| (26.1) chlorantraniliprole | 100 | 0 | |
| (26.2) cyantraniliprole | 200 | 18 | |
| | 100 | 0 | |
| (2B.2) fipronil | 200 | 8 | |
| (27.27) sulfoxaflor | 100 | 0 | |
| (I-1) + (4A.6) 1:4 | 50 + 200 | 73 | 32 |
| (I-1) + (4A.2) 1:4 | 50 + 200 | 50 | 29 |
| (I-1) + (4A.2) 1:2 | 50 + 100 | 51 | 29 |
| (I-1) + (4A.7) 1:4 | 50 + 200 | 73 | 47 |
| (I-1) + (4A.7) 1:2 | 50 + 100 | 53 | 42 |
| (I-1) + (26.1) 1:2 | 50 + 100 | 68 | 29 |
| (I-1) + (26.2) 1:4 | 50 + 200 | 55 | 42 |
| (I-1) + (26.2) 1:2 | 50 + 100 | 54 | 29 |
| (I-1) + (2B.2) 1:4 | 50 + 200 | 54 | 35 |
| (I-1) + (27.27) 1:2 | 50 + 100 | 52 | 29 |

*found = activity found
**calc. = activity calculated using Colby's formula

TABLE L2

Venturia test (apples)/preventive

| Active compounds | Application rate of active compound in ppm a.i. | Efficacy in % found* | calc.** |
|---|---|---|---|
| (I-1) 2,6-dimethyl-1H,5H-[1,4]dithiino[2,3-c:5,6-c']dipyrrole-1,3,5,7(2H,6H)-tetrone | 12.5 | 33 | |
| 6.1 abamectin | 200 | 51 | |
| | 100 | 53 | |
| 3A.43 tefluthrin | 100 | 23 | |
| 1A.15 methiocarb | 100 | 4 | |
| 27.16 4-{[(6-chloropyridin-3-yl)methyl](2,2-difluoroethyl)amino}furan-2(5H)-one | 200 | 8 | |
| (I-1) 2,6-dimethyl-1H,5H-[1,4]dithiino[2,3-c:5,6-c']dipyrrole-1,3,5,7(2H,6H)-tetrone | 12.5 | 33 | |
| 6.1 abamectin | 200 | 51 | |
| | 100 | 53 | |
| 3A.43 tefluthrin | 100 | 23 | |
| 1A.15 methiocarb | 100 | 4 | |
| 27.16 4-{[(6-chloropyridin-3-yl)methyl](2,2-difluoroethyl)amino}furan-2(5H)-one | 200 | 8 | |
| (I-1) + 6.1 1:16 | 12.5 + 200 | 93 | 67 |
| (I-1) + 6.1 1:8 | 12.5 + 100 | 79 | 69 |
| (I-1) + 3A.43 1:8 | 12.5 + 100 | 58 | 48 |
| (I-1) + 1A.15 1:8 | 12.5 + 100 | 61 | 36 |
| (I-1) + 27.16 1:16 | 12.5 + 200 | 77 | 38 |

*found = activity found
**calc. = activity calculated using Colby's formula

The invention claimed is:
1. A composition comprising
(A) at least one dithiino-tetracarboximide of formula (I)

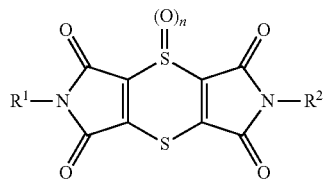

in which $R^1$ and $R^2$ are identical and represent methyl, ethyl, n-propyl or isopropyl, and n represents 0 or 1, or an agrochemically acceptable salt thereof,
and
(B) at least one further active compound selected from the following groups
  (1) acetylcholinesterase (AChE) inhibitors,
  (2) GABA-gated chloride channel antagonists,
  (3) sodium channel modulators/voltage-dependent sodium channel blockers,
  (4) nicotinergic acetylcholine receptor agonists,
  (5) allosteric acetylcholine receptor modulators (agonists),
  (6) chloride channel activators,
  (7) juvenile hormone mimics,
  (8) miscellaneous non-specific (multi-site) inhibitors,
  (9) selective homopteran feeding blockers,
  (10) mite growth inhibitors,
  (11) microbial disruptors of insect midgut membranes,
  (12) inhibitors of mitochondrial ATP synthase,
  (13) uncouplers of oxidative phosphorylation via disruption of the proton gradient,
  (14) nicotinic acetylcholine receptor channel blockers,
  (15) inhibitors of chitin biosynthesis (type 0),
  (16) inhibitors of chitin biosynthesis (type 1),
  (17) moulting disruptors,
  (18) ecdysone receptor agonists/disruptors,
  (19) octopamine receptor agonists,
  (20) mitochondrial complex III electron transport inhibitors,
  (21) mitochondrial complex I electron transport inhibitors,
  (22) voltage-dependent sodium channel blockers,
  (23) inhibitors of acetyl CoA carboxylase,
  (24) mitochondrial complex IV electron inhibitors,
  (25) mitochondrial complex II electron transport inhibitors,
  (26) ryanodine receptor modulators,
  (27) other insecticides.

2. The composition according to claim 1, wherein the compound of the formula (I) is (I-1) 2,6-dimethyl-1H,5H-[1,4]dithiino[2,3-c:5,6-c']dipyrrole-1,3,5,7(2H,6H)-tetrone.

3. The composition according to claim 1 further comprising auxiliaries, solvents, carriers, surfactants or extenders.

4. A method for controlling phytopathogenic fungi and/or animal pests in crop protection, comprising applying the composition according to claim 1 to seed, to a plant, to a fruit of the plant, or to soil on which the plant grows or soil from which the seed, the plant, or the fruit of the plant grows.

5. The method according to claim 4 wherein the composition is applied to the soil on which the seed, the plant, or the fruit of the plant grows or from which the seed, the plant, or the fruit of the plant grows.

6. The method according to claim 4, wherein the composition is applied as a foliar treatment.

7. The method according to claim 6 wherein the composition is applied at a rate from 0.1 to 10 000 g/ha.

8. The method according to claim 4 wherein the composition is applied to the seed.

9. The method according to claim 8 wherein the composition is applied at rate of from 2 g to 200 g per 100 kg of seed.

10. The method according to claim 4 wherein the plant is a transgenic plant.

11. The method according to claim 4 wherein the seed is seed of a transgenic plant.

12. The composition according to claim 1 wherein the at least one dithiino-tetracarboximide and the least one further active compound are present in a synergistically effective weight ratio.

13. The composition according to claim 12 wherein the at least one dithiino-tetracarboximide and the least one further active compound are present in a weight ratio of 250:1 to 1:250.

14. The composition according to claim 12 wherein the at least one dithiino-tetracarboximide and the at least one further active compound are present in a weight ratio of 125:1 to 1:125.

15. The composition according to claim 12 wherein the at least one dithiino-tetracarboximide and the at least one further active compound are present in a weight ratio of 50:1 to 1:50.

16. The composition according to claim 13 wherein the at least one dithiino-tetracarboximide and the at least one further active compound are present in a weight ratio of 20:1 to 1:20.

17. The composition according to claim 1 further comprising seed.

* * * * *